US010086050B2

(12) United States Patent
Clark et al.

(10) Patent No.: US 10,086,050 B2
(45) Date of Patent: Oct. 2, 2018

(54) TREATING INFECTION

(71) Applicants: University of Southampton, Hampshire (GB); University of Cape Town, Cape Town (ZA)

(72) Inventors: Howard William Clark, Hampshire (GB); William Horsnell, Cape Town (ZA)

(73) Assignees: University of Southampton, Hampshire (GB); University of Cape Town, Cape Town (ZA)

(*) Notice: Subject to any disclaimer, the term of this patent is extended or adjusted under 35 U.S.C. 154(b) by 0 days.

(21) Appl. No.: 15/120,007

(22) PCT Filed: Feb. 19, 2015

(86) PCT No.: PCT/GB2015/050474
§ 371 (c)(1),
(2) Date: Aug. 18, 2016

(87) PCT Pub. No.: WO2015/124928
PCT Pub. Date: Aug. 27, 2015

(65) Prior Publication Data
US 2017/0056481 A1    Mar. 2, 2017

(30) Foreign Application Priority Data
Feb. 19, 2014  (GB) .................................. 1402909.4

(51) Int. Cl.
| C07K 14/78 | (2006.01) |
| A61K 38/17 | (2006.01) |
| A61K 35/62 | (2006.01) |
| C07K 14/785 | (2006.01) |
| G01N 33/53 | (2006.01) |
| A61K 45/06 | (2006.01) |
| G01N 33/68 | (2006.01) |

(52) U.S. Cl.
CPC ............ *A61K 38/395* (2013.01); *A61K 35/62* (2013.01); *A61K 45/06* (2013.01); *C07K 14/785* (2013.01); *G01N 33/5308* (2013.01); *G01N 33/6896* (2013.01); *G01N 2333/43526* (2013.01); *G01N 2333/785* (2013.01); *G01N 2800/122* (2013.01); *G01N 2800/26* (2013.01)

(58) Field of Classification Search
CPC .............................. C07K 14/785; A61K 38/395
See application file for complete search history.

(56) References Cited

U.S. PATENT DOCUMENTS

2008/0255043 A1   10/2008 Mahajan et al.

FOREIGN PATENT DOCUMENTS

| WO | WO 2000/23569 A1 | 4/2000 |
| WO | WO 2003/035679 A2 | 5/2003 |
| WO | WO 2003/038058 A2 | 5/2003 |
| WO | WO 2004/091436 A2 | 10/2004 |
| WO | WO 2004/110143 A2 | 12/2004 |
| WO | WO 2007/076868 A2 | 7/2007 |

OTHER PUBLICATIONS

Thawer et al. Feb. 22, 2016; Surfactant protein-D is essential for immunity to helminth infection. PLoS Pathogens. 12(2): e1005461.*
Atochina, E.N. et al.; "Delayed Clearance of *Pneumocystis carinii* Infection, Increased Inflammation, and Altered Nitric Oxide Metabolism in Lungs of Surfactant Protein-D Knowckout Mice"; Journal of Infectious Diseases, vol. 189, No. 8; Mar. 30, 2004; pp. 1528-1539.
Altschul, S.F.; "Basic local alignment search tool"; downloaded from the Internet on Nov. 10, 2016 at http://www.sciencedirect.com/science/article/pii/S0022283605803602; Journal of Molecular Biology, vol. 215, Issue 3; Oct. 5, 1990; pp. 403-410.
Crouch, E. et al.; "Genomic Organization of Human Surfactant Protein D (SP-D)"; The Journal of Biological Chemistry, vol. 268, No. 4; Feb. 5, 1993; pp. 2976-2983.
Devereux, J. et al.; "A comprehensive set of sequence analysis programs for the VAX"; Nucleic Acids Research, vol. 12, No. 1; Jan. 11, 1984; pp. 387-395.
Koenraad van de Wetering, J. et al.; "Suractant Protein D Binding to Terminal α1-3-Linked Fucose Residues and to *Schistosoma mansoni*"; American Journal of Respiratory Cell and Molecular Biology, vol. 31, No. 5; Nov. 2004; pp. 565-572.
Lu, J. et al.; "Purification, characterization and cDNA cloning of human lung surfactant protein D"; Biochem. J., vol. 284; Jun. 15, 1992; pp. 795-802.
O'Riordan, D.M.; "Surfactant Protein D Interacts with *Pneumocystis carinii* and Mediates Organism Adherence to Alveolar Macrophages"; The Journal of Clinical Investigation, Inc., vol. 95; Jun. 1995; pp. 2699-2710.
Vuk Pavlovic, Z. et al.; "The role of Surfactant Protein D in Pneumocystis infection"; FASEB Journal, vol. 18, No. 4-5; Mar. 2004; one page; and presented at FASEB Meeting on Experimental Biology: Translating the Genome; Washington, D.C., Apr. 17-21, 2004.
International Search Report completed Apr. 27, 2015 for International Application No. PCT/GB2015/050474.
Written Opinion completed Apr. 27, 2015 for International Application No. PCT/GB2015/050474.
Ausubel F.M. et al.; Short Protocols in Molecular Biology, Fourth Edition; John Wiley & Sons, Inc.; Chapter 18; 1999.
Ausubel F.M. et al.; Short Protocols in Molecular Biology, Fourth Edition; John Wiley & Sons, Inc.; pp. 7-58 to 7-60; 1999.

(Continued)

*Primary Examiner* — Karen Cochrane Carlson
(74) *Attorney, Agent, or Firm* — Brinks Gilson & Lione

(57) ABSTRACT

The present invention relates to Surfactant Protein D (SP-D) or nucleic acids encoding SP-D or variants thereof such as surfactant protein A or mannan binding lectin for use in the treatment and/or prevention of a parasitic infection. Methods for determining the presence of a parasitic infection by determining levels of SP-D in a sample are also disclosed. Also disclosed are helminths for treating allergy, inflammation or infection.

14 Claims, 8 Drawing Sheets
Specification includes a Sequence Listing.

(56) References Cited

OTHER PUBLICATIONS

Chow et al.; Measurements of Phagocytosis and Phagosomal Maturation; Current Protocols in Cell Biology, Unit 15.7, Supplement 22; 33 pages; May 2004.
Crouch, E. C.; "Surfactant protein-D and pulmonary host defense"; Respiratory Research, vol. 1; pp. 93-108; Aug. 25, 2000.
GenBank accession Nos. NM_003019.1; "*Homo sapiens* surfactant, pulmonary-associated protein D (SFTPD), mRNA"; Oct. 31, 2000.
GenBank accession No. XM_005776.2; "*Homo sapiens* surfactant, pulmonary-associated protein D (SFTPD), mRNA"; May 8, 2002.
GenBank accession No. X65018.1; "*H. sapiens* mRNA for lung surfactant protein D"; Apr. 10, 1995.
GenBank accession No. L05485.1; "Human surfactant protein D (SP-D) gene exon 7, complete cds"; Jan. 13, 1995.
Kölble, K. et al.; "Assignment of the Human Pulmonary Surfactant Protein D Gene (SFTP4) to 10q22-q23 Close to the Surfactant Protein A Gene Cluster"; Genomics, vol. 17; 294-298; Aug. 1993.
Rust, K. et al.; "Human Surfactant Protein D: SP-D Contains a C-Type Lectin Carbohydrate Recognition Domain"; Archives of Biochemistry and Biophysics, vol. 290, No. 1; pp. 116-126; Oct. 1991.
Van de Wetering J.K. et al.; "Surface Protein D Binding to Terminal α1-3-linked Fucose Residues and to *Schistosoma mansoni*"; American Journal of Respiratory Cell and Molecular Biology, vol. 31; pp. 565-572; XP055184876; Nov. 2004.

\* cited by examiner

SEQUENCE LISTING

<160> NUMBER OF SEQ ID NOS: 11

<210> SEQ ID NO 1
<211> LENGTH: 375
<212> TYPE: PRT
<213> ORGANISM: Homo sapiens

<400> SEQUENCE: 1

```
Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Ala Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205
```

```
Ile Pro Gly Asp Lys Gly Ala Lys Gly Glu Ser Gly Leu Pro Asp Val
    210                 215                 220
Ala Ser Leu Arg Gln Gln Val Glu Ala Leu Gln Gly Gln Val Gln His
225                 230                 235                 240
Leu Gln Ala Ala Phe Ser Gln Tyr Lys Lys Val Glu Leu Phe Pro Asn
                245                 250                 255
Gly Gln Ser Val Gly Glu Lys Ile Phe Lys Thr Ala Gly Phe Val Lys
                260                 265                 270
Pro Phe Thr Glu Ala Gln Leu Leu Cys Thr Gln Ala Gly Gly Gln Leu
            275                 280                 285
Ala Ser Pro Arg Ser Ala Ala Glu Asn Ala Ala Leu Gln Gln Leu Val
        290                 295                 300
Val Ala Lys Asn Glu Ala Ala Phe Leu Ser Met Thr Asp Ser Lys Thr
305                 310                 315                 320
Glu Gly Lys Phe Thr Tyr Pro Thr Gly Glu Ser Leu Val Tyr Ser Asn
                325                 330                 335
Trp Ala Pro Gly Glu Pro Asn Asp Asp Gly Ser Glu Asp Cys Val
                340                 345                 350
Glu Ile Phe Thr Asn Gly Lys Trp Asn Asp Arg Ala Cys Gly Glu Lys
            355                 360                 365
Arg Leu Val Val Cys Glu Phe
    370                 375

<210> SEQ ID NO 2
<211> LENGTH: 1128
<212> TYPE: DNA
<213> ORGANISM: Homo sapiens

<400> SEQUENCE: 2
atgctgctct tcctcctctc tgcactggtc ctgctcacac agcccctggg ctacctggaa      60
gcagaaatga agacctactc ccacagaaca atgcccagtg cttgcaccct ggtcatgtgt     120
agctcagtgg agagtggcct gcctggtcgc gatggacggg atgggagaga gggccctcgg     180
ggcgagaagg gggacccagg tttgccagga gctgcagggc aagcagggat gcctggacaa     240
gctggcccag ttgggccaaa aggggacaat ggctctgttg agaacctgga ccaaaggga      300 gacactgggc caagtggacc tccaggacct cccggtgtgc ctggtccagc tggaagagaa     360
ggtgccctgg ggaagcaggg gaacatagga cctcagggca agccaggccc aaaaggagaa     420
gctgggccta aggagaagt aggtgcccca ggcatgcagg gctcggcagg gcaagaggc      480 ctcgcaggcc ctaagggaga gcgaggtgtc cctggtgagc gtggagtccc tggaaacaca     540
ggggcagcag ggtctgctgg agccatgggt ccccagggaa gtccaggtgc aggggacccc    600
ccgggattga agggggacaa aggcattcct ggagacaaag gagcaaaggg agaaagtggg     660
cttccagatg ttgcttctct gaggcagcag gttgaggcct acagggaca agtacgcac      720 ctccaggctg ctttctctca gtataagaaa gttgagctct cccaaatgg ccaaagtgtg     780 ggggagaaga tttcaagac agcaggcttt gtaaaccat ttacggaggc acagctgctg     840
tgcacacagg ctggtggaca gttggcctct ccacgctctg ccgctgagaa tgccgccttg     900
caacagctgg tcgtagctaa gaacgaggct gctttcctga gcatgactga ttccaagaca     960
gagggcaagt tcacctaccc cacaggagag tccctggtct attccaactg ggccccaggg    1020
gagcccaacg atgatggcgg gtcagaggac tgtgtggaga tcttcaccaa tggcaagtgg    1080
aatgacaggg cttgtggaga aaagcgtctt gtggtctgcg agttctga                 1128
```

<210> SEQ ID NO 3
<211> LENGTH: 177
<212> TYPE: PRT
<213> ORGANISM: Artificial Sequence
<220> FEATURE:
<223> OTHER INFORMATION: Recombinant fraction of human SP-D (rfhSP-D)

<400> SEQUENCE: 3

Gly Ser Pro Gly Leu Lys Gly Asp Lys Gly Ile Pro Gly Asp Lys Gly
1               5                   10                  15

Ala Lys Gly Glu Ser Gly Leu Pro Asp Val Ala Ser Leu Arg Gln Gln
            20                  25                  30

Val Glu Ala Leu Gln Gly Gln Val Gln His Leu Gln Ala Ala Phe Ser
        35                  40                  45

Gln Tyr Lys Lys Val Glu Leu Phe Pro Asn Gly Gln Ser Val Gly Glu
    50                  55                  60

Lys Ile Phe Lys Thr Ala Gly Phe Val Lys Pro Phe Thr Glu Ala Gln
65                  70                  75                  80

Leu Leu Cys Thr Gln Ala Gly Gly Gln Leu Ala Ser Pro Arg Ser Ala
                85                  90                  95

Ala Glu Asn Ala Ala Leu Gln Gln Leu Val Val Ala Lys Asn Glu Ala
            100                 105                 110

Ala Phe Leu Ser Met Thr Asp Ser Lys Thr Glu Gly Lys Phe Thr Tyr
        115                 120                 125

Pro Thr Gly Glu Ser Leu Val Tyr Ser Asn Trp Ala Pro Gly Glu Pro
    130                 135                 140

Asn Asp Asp Gly Gly Ser Glu Asp Cys Val Glu Ile Phe Thr Asn Gly
145                 150                 155                 160

Lys Trp Asn Asp Arg Ala Cys Gly Glu Lys Arg Leu Val Val Cys Glu
                165                 170                 175

Phe

<210> SEQ ID NO 4
<211> LENGTH: 534
<212> TYPE: DNA
<213> ORGANISM: Artificial Sequence
<220> FEATURE:
<223> OTHER INFORMATION: Nucleic acid encoding rfhSP-D

<400> SEQUENCE: 4
ggaagcccgg gattgaaggg ggacaaaggc attcctggag acaaaggagc aaagggagaa      60
agtgggcttc cagatgttgc ttctctgagg cagcaggttg aggccttaca gggacaagta     120
cagcacctcc aggctgcttt ctctcagtat aagaaagttg agctcttccc aaatggccaa     180
agtgtggggg agaagatttt caagacagca ggctttgtaa aaccatttac ggaggcacag     240
ctgctgtgca cacaggctgg tggacagttg gcctctccac gctctgccgc tgagaatgcc     300
gccttgcaac agctggtcgt agctaagaac gaggctgctt tcctgagcat gactgattcc     360
aagacagagg gcaagttcac ctaccccaca ggagagtccc tggtctattc caactgggcc     420
ccaggggagc ccaacgatga tgcgggtca gaggactgtg tggagatctt caccaatggc     480
aagtggaatg acagggcttg tggagaaaag cgtcttgtgg tctgcgagtt ctga          534

<210> SEQ ID NO 5
<211> LENGTH: 125
<212> TYPE: PRT
<213> ORGANISM: Artificial Sequence

```
<220> FEATURE:
<223> OTHER INFORMATION: Head region or carbohydrate recognition domain
      of SP-D

<400> SEQUENCE: 5

Val Glu Leu Phe Pro Asn Gly Gln Ser Val Gly Glu Lys Ile Phe Lys
1               5                   10                  15

Thr Ala Gly Phe Val Lys Pro Phe Thr Glu Ala Gln Leu Leu Cys Thr
            20                  25                  30

Gln Ala Gly Gly Gln Leu Ala Ser Pro Arg Ser Ala Ala Glu Asn Ala
        35                  40                  45

Ala Leu Gln Gln Leu Val Val Ala Lys Asn Glu Ala Ala Phe Leu Ser
    50                  55                  60

Met Thr Asp Ser Lys Thr Glu Gly Lys Phe Thr Tyr Pro Thr Gly Glu
65                  70                  75                  80

Ser Leu Val Tyr Ser Asn Trp Ala Pro Gly Glu Pro Asn Asp Asp Gly
                85                  90                  95

Gly Ser Glu Asp Cys Val Glu Ile Phe Thr Asn Gly Lys Trp Asn Asp
            100                 105                 110

Arg Ala Cys Gly Glu Lys Arg Leu Val Val Cys Glu Phe
        115                 120                 125

<210> SEQ ID NO 6
<211> LENGTH: 28
<212> TYPE: PRT
<213> ORGANISM: Artificial Sequence
<220> FEATURE:
<223> OTHER INFORMATION: Neck region of SP-D polypeptide

<400> SEQUENCE: 6

Asp Val Ala Ser Leu Arg Gln Gln Val Glu Ala Leu Gln Gly Gln Val
1               5                   10                  15

Gln His Leu Gln Ala Ala Phe Ser Gln Tyr Lys Lys
            20                  25

<210> SEQ ID NO 7
<211> LENGTH: 24
<212> TYPE: PRT
<213> ORGANISM: Artificial Sequence
<220> FEATURE:
<223> OTHER INFORMATION: N-terminal sequence of SP-D

<400> SEQUENCE: 7

Gly Ser Pro Gly Leu Lys Gly Asp Lys Gly Ile Pro Gly Asp Lys Gly
1               5                   10                  15

Ala Lys Gly Glu Ser Gly Leu Pro
            20

<210> SEQ ID NO 8
<211> LENGTH: 248
<212> TYPE: PRT
<213> ORGANISM: Homo sapiens

<400> SEQUENCE: 8

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45
```

```
Gly Leu Lys Gly Asp Pro Gly Pro Pro Gly Pro Met Gly Pro Pro Gly
 50                  55                  60

Glu Met Pro Cys Pro Pro Gly Asn Asp Gly Leu Pro Gly Ala Pro Gly
 65                  70                  75                  80

Ile Pro Gly Glu Cys Gly Glu Lys Gly Glu Pro Gly Glu Arg Gly Pro
                 85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 9
<211> LENGTH: 2230
<212> TYPE: DNA
<213> ORGANISM: Homo sapiens

<400> SEQUENCE: 9
gacttggagg cagagaccca agcagctgga ggctctgtgt gtgggtcgct gatttcttgg      60
agcctgaaaa gaaagtaaca cagcagggat gaggacagat ggtgtgagtc agtgagagca     120
gcgactggac ccagagccat gtggctgtgc cctctggccc tcaacctcat cttgatggca     180
gcctctggtc tgtgtgcgca agtgaaggac gtttgtgttg aagccctggg tatccccggc     240
actcctggat cccacggcct gccaggcagg gacgggagag atggtctcaa aggagaccct     300
ggccctccag gccccatggg tccacctgga gaaatgccat gtcctcctgg aaatgatggg     360
ctgcctggag ccctggtat cccctggagag tgtggagaga aggggagcc tggcgagagg      420 ggccctccag ggcttccagc tcatctagat gaggagctcc aagccacact ccacgacttt     480
agacatcaaa tcctgcagac aaggggagcc ctcagtctgc agggctccat aatgacagta     540
ggagagaagg tcttctccag caatgggcag tccatcactt ttgatgccat tcaggaggca     600
tgtgccagag caggcggccg cattgctgtc ccaaggaatc cagaggaaaa tgaggccatt     660
gcaagcttcg tgaagaagta caacacatat gcctatgtag gcctgactga gggtcccagc     720
cctggagact tccgctactc agacgggacc cctgtaaact acaccaactg gtaccgaggg     780
gagcccgcag gtcggggaaa agagcagtgt gtggagatgt acacagatgg cagtggaat      840 gacaggaact gcctgtactc ccgactgacc atcgtgagt tctgagaggc atttaggcca      900
tgggacaggg aggacgctct ctggccttcg gcctccatcc tgaggctcca cttggtctgt     960
```

```
gagatgctag aactcccttt caacagaatt cacttgtggc tattgggact ggaggcaccc    1020
ttagccactt cattcctctg atgggccctg actcttcccc ataatcactg accagccttg    1080
acactcccct tgcaaactct cccagcactg caccccaggc agccactctt agccttggcc    1140
ttcgacatga gatggagccc tccttattcc ccatctggtc cagttccttc acttacagat    1200
ggcagcagtg aggtcttggg gtagaaggac cctccaaagt cacacaaagt gcctgcctcc    1260
tggtcccctc agctctctct ctgcaaccca gtgccatcag gatgagcaat cctgccaag     1320 cataatgaca gagagaggca gacttcgggg aagccctgac tgtgcagagc taaggacaca    1380
gtggagattc tctggcactc tgaggtctct gtggcaggcc tggtcaggct ctccatgagg    1440
ttagaaggcc aggtagtgtt ccagcagggt ggtggccaag ccaaccccat gattgatgtg    1500
tacgattcac tcctttgagt ctttgaatgg caactcagcc ccctgacctg aagacagcca    1560
gcctaggcct ctagggtgac ctagagccgc cttcagatgt gacccgagta actttcaact    1620
gatgaacaaa tctgcaccct acttcagatt tcagtgggca ttcacaccac ccccacacc     1680 actggctctg ctttctcctt tcattaatcc attcacccag atatttcatt aaaattatca    1740
cgtgccaggt cttaggatat gtcgtggggt gggcaaggta atcagtgaca gttgaagatt    1800 ttttttttccc agagcttatg tcttcatctg tgaaatggga ataagatact tgttgctgtc    1860
acagttatta ccatcccccc agctaccaaa attactacca gaactgttac tatacacaga    1920
ggctattgac tgagcaccta tcatttgcca agaaccttga caagcacttc taatacagca    1980
tattatgtac tattcaatct ttacacaatg tcacgggacc agtattgttt cctcattttt    2040
tataaggaca ctgaagcttg gaggagttaa atgtttttgag tattattcca gagagcaagt    2100
ggcagaggct ggatccaaac ccatcttcct ggacctgaag cttatgcttc cagccacccc    2160
actcctgagc tgaataaaga tgatttaagc ttaataaatc gtgaatgtgt tcacaaaaaa    2220
aaaaaaaaaa                                                           2230
```

<210> SEQ ID NO 10
<211> LENGTH: 248
<212> TYPE: PRT
<213> ORGANISM: Homo sapiens

<400> SEQUENCE: 10

```
Met Ser Leu Phe Pro Ser Leu Pro Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140
```

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
            245

<210> SEQ ID NO 11
<211> LENGTH: 3569
<212> TYPE: DNA
<213> ORGANISM: Homo sapiens

<400> SEQUENCE: 11

```
ggtaaatatg tgttcattaa ctgagattaa ccttccctga gttttctcac accaaggtga      60
ggaccatgtc cctgttttcca tcactccctc tccttctcct gagtatggtg gcagcgtctt     120
actcagaaac tgtgacctgt gaggatgccc aaaagacctg ccctgcagtg attgcctgta     180
gctctccagg catcaacggc ttcccaggca agatgggcg tgatggcacc aagggagaaa     240 aggggggaacc aggccaaggg ctcagaggct tacagggccc ccctggaaag ttggggcctc     300
caggaaatcc agggccttct gggtcaccag gaccaagggg ccaaaaagga gaccctggaa     360
aaagtccgga tggtgatagt agcctggctg cctcagaaag aaaagctctg caaacagaaa     420
tggcacgtat caaaaagtgg ctcaccttct ctctgggcaa acaagttggg aacaagttct     480
tcctgaccaa tggtgaaata atgaccttg aaaaagtgaa ggccttgtgt gtcaagttcc     540
aggcctctgt ggccaccccc aggaatgctg cagagaatgg agccattcag aatctcatca     600
aggaggaagc cttcctgggc atcactgatg agaagacaga agggcagttt gtggatctga     660
caggaaatag actgacctac acaaactgga acgagggtga acccaacaat gctggttctg     720
atgaagattg tgtattgcta ctgaaaaatg gccagtggaa tgacgtcccc tgctccacct     780
cccatctggc cgtctgtgag ttccctatct gaagggtcat atcactcagg ccctccttgt     840 cttttactg caacccacag gcccacagta tgcttgaaaa gataaattat atcaatttcc     900
tcatatccag tattgttcct tttgtgggca atcactaaaa atgatcacta acagcaccaa     960
caaagcaata atagtagtag tagtagttag cagcagcagt agtagtcatg ctaattatat    1020
aatattttta atatatacta tgaggcccta tcttttgcat cctacattaa ttatctagtt    1080
taattaatct gtaatgcttt cgatagtgtt aacttgctgc agtatgaaaa taagacggat    1140
ttatttttcc atttacaaca aacacctgtg ctctgttgag ccttcctttc tgtttgggta    1200
gagggctccc ctaatgacat caccacagtt taataccaca gcttttttacc aagtttcagg    1260 tattaagaaa atctattttg taactttctc tatgaactct gttttctttc taatgagata    1320
ttaaaccatg taaagaacat aaataacaaa tctcaagcaa acagcttcac aaattctcac    1380
acacatacat acctatatac tcactttcta gattaagata tgggacattt ttgactccct    1440
agaagccccg ttataactcc tcctagtact aactccttagg aaaatactat tctgacctcc    1500
```

```
atgactgcac agtaatttcg tctgtttata aacattgtat agttggaatc atattgtgtg      1560
taatgttgta tgtcttgttt actcagaatt aagtctgtga gattcattca tgtcatgtgt      1620
acaaaagttt catcctttc attgccatgt agggttccct tatattaata ttcctcagtt       1680
catccattct attgttaata ggcacttaag tggcttccaa ttttggcca tgaggaagag       1740 aacccacgaa cattcctgga cttgtctttt ggtggacatg gtgcactaat ttcactacct      1800
atccaggagt ggaactggta gaggatgagg aaagcatgta ttcagcttta gtagatatta     1860
ccagttttcc taagtgattg tatgaattta tgctcctacc ggcaatgtgt ggcagtccta     1920
gatgctctat gtgcttgtaa aaagtcaatg ttttcagttc tcttgatttt cattattcct    1980
gtggatgtaa agtgatattt ccccatggtt ttaatctgta tttccccaac atgtaataag   2040
gttgaacact tttttatatg cttattgggc acttgggtat cttcttttgt gaagtacccg    2100
ttcacatttt tgtattttgt ttaaattagt tagccaatat ttttcttact gatttttaag    2160 ttattttac attctgaata tgtccttttt aatgtgtatt acaaatattt tgctagtttt     2220
tgacttgctc ctaatgttga attttgatga acaaaatttc ctaattttga gaaagtctta    2280
tttattcata ttttctttca aaattagtgc tttttgtgtc atgtttaaga aatttttgcc    2340
catcccaaaa tcataagata ttttcatga ttttgaaacc atgaagagat ttttcatgat    2400
tttgaaatca tgaagatatt tttccatttt tttctaatag ttttattaat aaacattcta    2460
tctattcctg gtagaataga tatccacttg agacagcact atgtaggaaa gaccatttt    2520 cctccactga actagggtgg tgcattttg taagttaggt aactgtatgt gtgtgtgtct     2580
gtttctgggc tgtctattct agtctatttg ttgatgcttg tgtcaaacag tacactatct    2640
taattattgt acatttatag ttgtaactat agtccagctt tgttcttctt aaagtcaaga    2700
tttccatata aatattagaa acagcttctc aatttctaca aaatcctgat gaggtttcta    2760
ctgggaccac attgagtcta tcaatcaact tatgcagaac tggcaactta ctactgaatc    2820
tctaatcaat gttcatcatg tatcgcttca tgtaactaga attctttaa cttaattgct     2880 atgttttgac attttagtt taaaaaccct gtatatcttg ttttggtggt tttagtgatt    2940
ttaataatat atttaaata tttttctt tctattgttg tacacagaaa tacagttaag    3000
ttttgtgtgt agtcttacga tgtttagtaa actcaataag tttattcctt aaatctagta   3060
atttgtagat tcctctggat tttgtatatg catagtcatg taagctgaaa atatggcaat   3120
acttgcttct tcccaattgc tttacctttt ttcttacctt attgcactgg ttagcaaccc    3180
caatacagag accaccagat caggtataga ctcctgaaag acaatataat gaagtgctcc   3240
agtcaggcct atctaaactg gattcacagc tctgtcactt aattgctaca tgatctagag   3300
ccagttactt tgtgtttcag ccatgtattt gcagctgaga gaaaataatc attcttattt   3360
catgaaaatt gtggggatga tgaaataagt taacaccttt aaagtgtgta gtaaagtatc   3420
aggatactat attttaggtc ttaatacaca cagttatgcc gctagataca tgcttttaa   3480 tgagataatg tgatattata cataacacat atcgattttt aaaaattaaa tcaaccttgc   3540
tttgatggaa taaactccat ttagtcaca                                     3569
```

TREATING INFECTION

This application claims the benefit under 35 U.S.C. § 371 of International Application No. PCT/GB2015/050474, filed Feb. 19, 2015, which claims the benefit of Great Britain Application No. 1402909.4, filed Feb. 19, 2014, which are incorporated by reference herein in their entirety.

FIELD OF THE INVENTION

The present invention relates to the field of treatments for parasitic infection, especially parasitic nematode infections.

BACKGROUND TO THE INVENTION

Parasitic infections are major veterinary and public health problems. As an illustration, approximately one third of the world population is infected with a parasitic nematode at any one time. Infections in livestock typically lead to death and a loss of yield. In humans infections generally cause morbidity as opposed to death. The medical effects can be severe; including anaemia, impaired cognitive, physiological and immunological development.

Currently, treatment of nematode infections relies on a small range of pharmaceuticals. Resistance to these drugs is widespread in agriculture and emerging in humans. Resistance is currently a multi-billion dollar burden on agriculture and a potentially major medical problem.

Human infections are typically treated by administration of mebendazole and livestock are frequently treated empirically with mebendazole (or derivatives) or ivermectin. Such blanket drug administration underlies the widespread drug resistance problems in agriculture. No vaccines are presently available against parasitic nematode infections.

There is thus a need for alternative therapies for parasitic infections that are not associated with the disadvantages and problems mentioned above.

SUMMARY OF THE INVENTION

Accordingly, the present invention provides Surfactant Protein D (SP-D), or a fragment, homologue, variant or derivative thereof, for use in treatment and/or prevention of a parasitic infection in a subject.

In one embodiment, SP-D comprises the sequence shown in SEQ ID NO: 1, or the SP-D fragment, homologue, variant or derivative comprises an amino acid sequence having at least 70% sequence identity over at least 50 amino acid residues of SEQ ID NO:1.

In another embodiment, the SP-D fragment comprises the sequence shown in SEQ ID NO: 3, or the SP-D fragment, homologue, variant or derivative comprises an amino acid sequence having at least 70% sequence identity over at least 50 amino acid residues of SEQ ID NO:3.

In one embodiment, the present invention provides SP-A or mannan-binding lectin for use in treatment and/or prevention of a parasitic infection in a subject.

In one embodiment, SP-D, or the fragment, homologue, variant or derivative thereof, has carbohydrate binding activity.

In one embodiment, SP-D, or the fragment, homologue, variant or derivative thereof, reduces parasite burden in the subject.

In one embodiment, SP-D, or the fragment, homologue, variant or derivative thereof, enhances alternative activation of alveolar macrophages in the subject.

In one embodiment, SP-D, or the fragment, homologue, variant or derivative thereof, induces innate lymphoid type 2 cells.

In one embodiment, SP-D, or the fragment, homologue, variant or derivative thereof, acts as an opsonin of the parasite.

In one embodiment, a lifecycle of the parasite involves infestation of the lungs of the subject.

In one embodiment, the parasite is a parasitic helminth. In a preferred embodiment, the parasite is a parasitic nematode.

In one embodiment, the subject is a mammal.

In one embodiment, the SP-D, or the fragment, homologue, variant or derivative thereof, is administered to the lungs of the subject. In a preferred embodiment, the SP-D, or the fragment, homologue, variant or derivative thereof, is administered intranasally.

In one embodiment, the SP-D, or the fragment, homologue, variant or derivative thereof, is administered in combination with an anti-parasite therapy. Preferably the anti-parasite therapy is an anti-nematode therapy selected from the group consisting of albendazole, mebendazole, thiabendazole, ivermectin, piperazine, pyrantel pamoate, and levamisole.

In a further aspect, the invention provides a nucleic acid encoding SP-D, or a fragment, homologue, variant or derivative thereof, for use in treatment and/or prevention of a parasitic infection in a subject.

In another aspect, the invention provides a pharmaceutical composition comprising SP-D, or a fragment, homologue, variant or derivative thereof, for use in treatment and/or prevention of a parasitic infection in a subject.

In one embodiment, the composition further comprises a pharmaceutical excipient and/or carrier.

In a further aspect, the invention provides a method for treatment and/or prevention of a parasitic infection in a subject, comprising a step of administering SP-D, or a fragment, homologue, variant or derivative thereof, to the subject.

In a further aspect, the invention provides use of SP-D, or a fragment, homologue, variant or derivative thereof, in the manufacture of a medicament for treating and/or preventing a parasitic infection.

In a further aspect, the invention provides a method for determining the presence of a parasitic infection in a subject comprising the step of determining the level of SP-D in a sample from the subject, wherein increased levels of SP-D compared to a control sample indicate parasitic infection.

In another aspect, the invention provides the use of SP-D or a fragment, homologue, variant or derivative thereof in combination with helminth larva or a preparation thereof to enhance alternative activation of alveolar macrophages.

In another aspect the invention provides the use of SP-D or a fragment, homologue, variant or derivative thereof in combination with helminth larva or a preparation thereof to induce innate lymphoid type 2 cells.

The helminth larva or preparation thereof may be coated with SP-D or a fragment, homologue, variant or derivative thereof.

In a further aspect the present invention provides a composition comprising helminths for use in the prevention and/or treatment of allergy, lung inflammation or infection.

Administration of the composition increases levels of SP-D in a subject.

The composition may comprise whole helminths or a preparation thereof.

In a further aspect the invention provides the use of a helminth to induce innate lymphoid type 2 cells and/or to enhance alternative activation of alveolar macrophages.

DETAILED DESCRIPTION

Figure 1:
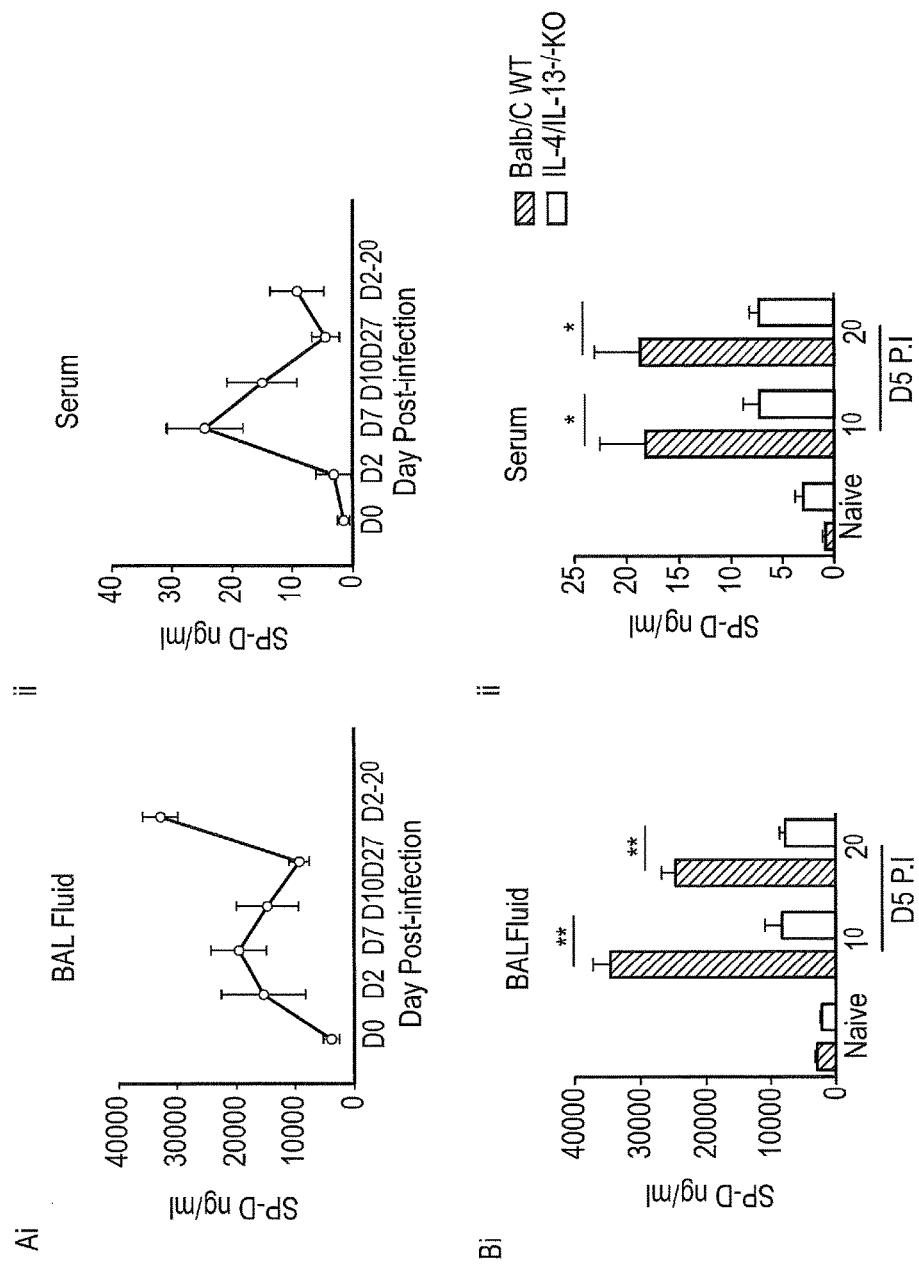
FIG. 1: SP-D is induced in the bronchoalveolar lavage fluid following Nb infection. (a) Kinetics of SP-D levels were measured by ELISA in (i) BAL fluid and (ii) Serum following Nb infection. (b) SP-D levels of WT and IL-4/IL-13$^{-/-}$ KO mice were measured in (i) BAL fluid and (ii) Serum in naïve mice and infected mice at day 5 post primary (1°) and secondary (2°) infection. Data are representative of one or two individual experiments. N=5 mice per group. *P<0.05, **P<0.01.

Embodiments of the present invention are based in part on the inventor's surprising determination that administration of SP-D to a subject with parasite infection reduces host parasite burden. SP-D mediates this function by direct interaction with both the host and the parasite.

Surfactant Protein D (SP-D)

In first aspect the present invention provides SP-D for use in the treatment and/or prevention of parasitic infection.

Surfactant Protein D has been identified and characterised previously, in for example Rust, et al (1991), Human surfactant protein D: SP-D contains a C-type lectin carbohydrate recognition domain. Archives of biochemistry and biophysics. 290 (1), 116-126; Lu, et al (1992) Purification, Characterization and cDNA Cloning of Human Lung Surfactant Protein D. Biochem. J. 284, 785-802; Crouch, et al (1993) Genomic organization of human surfactant protein D (SP-D). SP-D is encoded on chromosome 10q22.2-23.1. The Journal of biological chemistry. 268 (4), 2976-2983; Kolble, et al (1993) Assignment of the human pulmonary surfactant protein D gene (SFTP4) to 10q22-q23 close to the surfactant protein A gene cluster. Genomics. 17 (2), 294-298 (1993).

SP-D is 46 kDa hydrophilic calcium dependent, carbohydrate binding protein, classified under the collectin family of proteins. It is encoded by the long arm of human chromosome 10.

SP-D is secreted by Alveolar Epithelial Type II cells (ATII) cells, sub mucosal cells and Clara cells. It has its own secretory vesicle that extrudes from ATII cells into the alveolar lumen and associates with the underlying hydrophilic layer. Although the majority of SP-D is expressed in the lung, transcripts of SP-D have also been detected in other parts of the body, such as the intestine, thymus, prostrate, brain, testes, salivary gland, lachrymal gland and heart.

The basic structure of SP-D is organized into four regions: a cysteine containing N-terminal region, a triple-helical collagen region composed of Gly-X-Y triplets, an α-helical coiled coil neck region and a globular head region at the C-terminus consisting of a homotrimeric carbohydrate recognition domain (CRD). The SP-D is assembled as trimeric subunits of basic polypeptide chain which multimerize to varying degrees of oligomers but typically is found as a dodecamer. They are formed from the linking of four trimers by disulphide bonds at the N termini.

The carboxy-terminal domains have C-type (calcium-dependent) lectin activity that mediates the interaction of collectins with a wide variety of pathogens. This results in pathogen opsonization and enhanced uptake by phagocytes. The neck region has disulphide binding sites that form inter-chain bonds that are required for assembling the SP-D into trimers. The N-terminal domain confers structural stability on the protein, owing to its disulphide-bonding pattern and dictates the degree of multimerization of the single trimeric subunits.

In a steady state, SP-D has important functions in maintaining the surfactant homeostasis and normal physiology of the lung. SP-D enhances clearance and uptake of apoptotic cells by binding to cell debris and cell-surface DNA, thereby controlling inflammation, also plays an essential role for maintaining immunological homeostasis in the lung.

SP-D can directly bind to host immune cells and influence their response and phagocytic activity. SP-D displays chemotactic activity on neutrophils and certain mononuclear phagocytes and can induce directional actin polymerization in alveolar macrophages in a concentration dependent manner. It also modulates the production of cytokines and inflammatory mediators in a pathogen dependent manner.

Surfactant proteins (including SP-D) have also been shown to play protective role against lung infection, allergy, asthma and inflammation.

As used herein, Surfactant Protein D (SP-D) refers to any SP-D polypeptide or nucleic acid (as the context requires). These terms may refer to human SP-D, for example, the sequences disclosed in the above references, or in GenBank accession numbers NM_003019.1, XM_005776.2, X65018.1 and L05485.1.

The SP-D may be a human SP-D having the GenBank accession number NM_003019.1. The amino acid and nucleic acid sequences of such a human SP-D are shown in SEQ ID NO: 1 and SEQ ID NO: 2 respectively.

```
(Amino acid sequence of human SP-D (translated
from SEQ ID NO: 2))
                                         SEQ ID NO: 1
MLLFLLSALVLLTQPLGYLEAEMKTYSHRTMPSACTLVMCSSVESGLPGR

DGRDGREGPRGEKGDPGLPGAAGQAGMPGQAGPVGPKGDNGSVGEPGPKG

DTGPSGPPGPPGVPGPAGREGALGKQGNIGPQGKPGPKGEAGPKGEVGAP

GMQGSAGARGLAGPKGERGVPGERGVPGNTGAAGSAGAMGPQGSPGARGP

PGLKGDKGTPGDKGAKGESGLPDVASLRQQVEALQGQVQHLQAAFSQYKK

VELFPNGQSVGEKIFKTAGFVKPETEAQLLCTQAGGQLASPRSAAENAAL

QQLVVAKNEAAFLSMTDSKTEGKFTYPTGESLVYSNWAPGEPNDDGGSED

CVEIFTNGKWNDRACGEKRLVVCEF*

(Nucleotide sequence of human SP-D cDNA clone
(accession number NM_003019.1))
                                         SEQ ID NO: 2
ATGCTGCTCTTCCTCCTCTCTGCACTGGTCCTGCTCACACACCCCCTGGG

CTACCTGGAAGCAGAAATGAAGACCTACTCCCACAGAACAATGCCCAGTG

CTTGCACCCTGGTCATGTGTAGCTCAGTGGAGAGTGGCCTGCCTGGTCGC

GATGGACGGGATGGGAGAGAGGGCCCTCGGGGCGAGAAGGGGGACCCAGG

TTTGCCAGGAGCTGCAGGGCAAGCAGGGATGCCTGGACAAGCTGCCCAG

TTGGGCCAAAAGGGGACAATGGCTCTGTTGGAGAACCTGGACCAAAGGGA

GACACTGGGCCAAGTGGACCTCCAGGACCTCCCGGTGTGCCTGGTCCAGC

TGGAAGAGAAGGTGCCCTGGGGAAGCAGGGGAACATAGGACCTCAGGGCA

AGCCAGGCCCAAAAGGAGAAGCTGGGCCTAAAGGAGAAGTAGGTGCCCCA

GGCATGCAGGGCTCGGCAGGGGCAAGAGGCCTCGCAGGCCCTAAGGGAGA

GCGAGGTGTCCCTGGTGAGCGTGGAGTCCCTGGAAACACAGGGGCAGCAG

GGTCTGCTGGAGCCATGGGTCCCCAGGGAAGTCCAGGTGCCAGGGACCC

CCGGGATTGAAGGGGACAAAGGCATTCCTGGAGACAAAGGAGCAAAGGG

AGAAAGTGGGCTTCCAGATGTTGCTTCTCTGAGGCAGCAGGTTGAGGCCT

TACAGGGACAAGTACAGCACCTCCAGGCTGCTTTCTCTCAGTATAAGAAA

GTTGAGCTCTTCCCAAATGGCCAAAGTGTGGGGGAGAAGATTTTCAAGAC

AGCAGGCTTTGTAAAACCATTTACGGAGGCACAGCTGCTGTGCACACAGG
```

-continued
```
CTGGTGGACAGTTGGCCTCTCCACGCTCTGCCGCTGAGAATGCCGCCTTG

CAACAGCTGGTCGTAGCTAAGAACGAGGCTGCTTTCCTGAGCATGACTGA

TTCCAAGACAGAGGGCAAGTTCACCTACCCCACAGGAGAGTCCCTGGTCT

ATTCCAACTGGGCCCCAGGGGAGCCCAACGATGATGGCGGGTCAGAGGAC

TGTGTGGAGATCTTCACCAATGGCAAGTGGAATGACAGGGCTTGTGGAGA

AAAGCGTCTTGTGGTCTGCGAGTTCTGA
```

SP-D polypeptides for use according to the present invention include a fragment, homologue, variant or derivative of SP-D. Preferred fragments include those having one or more biological activities of SP-D.

The sequence of such a SP-D fragment was previously disclosed in WO 03/035679 and is shown herein as SEQ ID NO: 3 (rfhSP-D).

Furthermore, SP-D polypeptides also generally include any recombinant fragment of SP-D, preferably human SP-D, which lacks the N-terminal domain and/or the collagen domain, preferably both. Thus the SP-D polypeptide may be a recombinant fragment of SP-D, preferably human SP-D depicted in SEQ ID NO: 1, which lacks substantially lacks residues 1-178. The SP-D polypeptide may be a recombinant fragment of SP-D, preferably human SP-D sequence shown in SEQ ID NO: 1, comprising substantially residues 179-355.

The proline residue corresponding to position 200 of the human SP-D sequence (SEQ ID NO: 1) may be replaced by another residue. For example, the proline residue may be replaced with an uncharged polar residue, for example, a cysteine, serine, threonine or methionine residue. The proline residue may be replaced with a serine residue. Thus, the SP-D polypeptide may comprise a sequence shown in SEQ ID NO: 3 (rfhSP-D).

In preferred embodiments, the SP-D polypeptide comprises a "head" region or carbohydrate recognition domain (CRD), comprising substantially the following residues:

```
                                         SEQ ID NO: 5
VELFPNGQSVGEKIFKTAGFVKPFTEAQLLCTQAGGQLASPRSAAENAAL
QQLVVAKNEAAFLSMTDSKTEGKFTYPTGESLVYSNWAPGEPNDDGGSED
CVEIFTNGKWNDRACGEKRLVVCEF
```

Preferably, the SP-D polypeptide comprises means for multimerisation, preferably trimerisation, with another SP-D polypeptide. Such means may include for example, a biotin moiety which interacts with and binds to an avidin or streptavidin moiety on another SP-D polypeptide.

The SP-D polypeptide may further comprises a "neck" region comprising substantially the following residues:

DVASLRQQVEALQGQVQHLQAAFSQYKK (SEQ ID NO: 6)

Preferably, such a neck region is N terminal to the carbohydrate recognition domain CRD.

The SP-D polypeptide may further comprise at least one Gly-Xaa-Yaa stretch, preferably a sequence comprising a plurality of Gly-Xaa-Yaa repeats, most preferably a sequence comprising 8 Gly-Xaa-Yaa repeats. In a preferred embodiment, the SP-D polypeptide further comprises an N-terminal sequence comprising substantially GSPGLK-GDKGIPGDKGAKGESGLP (SEQ ID NO: 7).

The SP-D polypeptide may comprise a sequence shown in SEQ ID NO: 3 (rfhSP-D).

The SP-D polypeptide may consist of a sequence shown in SEQ ID NO: 3 (rfhSP-D).

(Amino acid sequence of rfhSP-D)
SEQ ID NO: 3
GSPGLKGDKGIPGDKGAKGESGIPDVASLRQQVEALQGQVQHLQAAFS

QYKKVELFPNGQSVGEKIFKTAGFVKPFTEAQLLCTQAGGQLASPRSAA

ENAALQQLVVAKNEAAFLSMTDSKTEGKFTYPTGESLVYSNWAPGEPND

DGGSEDCVEIFTNGKWNDRACGEKRLVVCEF

The SP-D, SP-D polypeptide or SP-D fragment for use according to the present invention also includes homologous sequences obtained from any source, for example related viral/bacterial proteins, cellular homologues and synthetic peptides, as well as variants or derivatives thereof. Thus polypeptides also include those encoding homologues of SP-D/rfhSP-D from other species including animals such as mammals (e.g. mice, rats or rabbits), especially primates, more especially humans. More specifically, homologues include human homologues.

Thus, the SP-D for use according to the present invention may be a variant, homologue or derivative of the amino acid sequence of the SP-D sequence shown in SEQ ID NO: 1 or the rfhSP-D sequence shown in SEQ ID NO: 3, as well as a variant, homologue or derivative of a nucleotide sequence encoding such amino acid sequences.

The SP-D polypeptide, variant, homologue, fragment or derivative for use according to the present invention provides one or more of the biological activities of SP-D. Thus, the variants etc. provide one or more activities including but not limited to, carbohydrate binding activity, multimerisation activity, including trimerisation activity, alternative activation of alveolar macrophages, induction of innate lymphoid type 2 cells and opsonisation of parasites, as well as any of the biological activities or properties disclosed in the Examples.

The SP-D polypeptide, variant, homologue, fragment or derivative for use according to the present invention reduces parasite burden in a host infected with the parasite and/or reduces the risk of a subject contracting the parasite.

As used herein, a homologous sequence is taken to include an amino acid sequence which is at least 15, 20, 25, 30, 40, 50, 60, 70, 80 or 90% identical, preferably at least 95 or 98% identical at the amino acid level over at least 50 or 100, preferably 200, 300, 400 or 500 amino acids with the sequence of SP-D shown in SEQ ID NO: 1. In particular, homology should typically be considered with respect to those regions of the sequence known to be essential for protein function rather than non-essential neighbouring sequences. This is especially important when considering homologous sequences from distantly related organisms.

Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These publicly and commercially available computer programs can calculate % homology between two or more sequences. % homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences for use according to the present invention includes any substitution of, variation of, modification of, replacement of, deletion of or addition of one (or more) amino acids from or to the sequence providing the resultant amino acid sequence retains substantially the same activity as the unmodified sequence, preferably having at least the same activity as the SP-D polypeptide shown in SEQ ID NO: 1.

Polypeptides having the amino acid sequence shown in the Examples, or fragments or homologues thereof may be modified for use as described herein. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Functional domains of SP-D include the collagen domain, the neck region and the carbohydrate recognition domain. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The SP-D polypeptides, variants, homologues, fragments and derivatives for use as described herein may be in a substantially isolated form. It will be understood that such polypeptides may be mixed with carriers or diluents which will not interfere with the intended purpose of the protein and still be regarded as substantially isolated. A SP-D variant, homologue, fragment or derivative may also be in a substantially purified form, in which case it will generally comprise the protein in a preparation in which more than 90%, e.g. 95%, 98% or 99% of the protein in the preparation is a protein.

Variants, homologues, fragments or derivatives of SP-D for use according to the present invention may encompass related polypeptides which provide one or more of the biological activities of SP-D. Thus, the variants etc. may provide one or more activities including but not limited to, carbohydrate binding activity, multimerisation activity, including trimerisation activity, alternative activation of alveolar macrophages, induction of innate lymphoid type 2 cells and opsonisation of parasites, as well as any of the biological activities or properties disclosed in the Examples.

The variant etc. may be, for example, Surfactant protein A (SP-A) or mannan-binding lectin.

SP-A is an innate immune system collectin which has collagen-like domains that are very similar to SP-D. It is primarily expressed in the lungs and facilitates phagocytosis by alveolar macrophages through opsonisation.

A SP-A polypeptide, variant, homologue, fragment or derivative for use according to the present invention may be a human SP-A having the GenBank accession number NM_005411. The variant, homologue, fragment or derivative of SP-A may be as defined in the same manner as a SP-D variant, homologue, fragment or derivative.

The amino acid and nucleic acid sequences of such a human SP-A are shown in SEQ ID NO: 8 and SEQ ID NO: 9 respectively.

SEQ ID NO: 8
MWLCPLALNLILMAASGAVCEVKDVCVGSPGIPGTPGSHGLPGRDGRDGL

KGDPGPPGPMGPPGEMPCPPGNDGLPGAPGIPGECGEKGEPGERGPPGLP

AHLDEELQATLHDFRHQILQTRGALSLQGSIMTVGEKVFSSNGQSITFDA

IQEACARAGGRIAVPRNPEENEAIASFVKKYNTYAYVGLTEGPSPGDFRY

SDGTPVNYTNWYRGEPAGRGKEQCVEMYTDGQWNDRNCLYSRLTICEF

The amino acid sequence of SP-A may be lacking the signal sequence (e.g. the amino acid sequence may lack residues 1 to 20 of SEQ ID NO: 8.

SEQ ID NO: 9
GACTTGGAGG CAGAGACCCA AGCAGCTGGA GGCTCTGTGT

GTGGGTCGCT GATTTCTTGG AGCCTGAAAA GAAAGTAACA

CAGCAGGGAT GAGGACAGAT GGTGTGAGTC AGTGAGAGCA

GCGACTGGAC CCAGAGCCAT GTGGCTGTGC CCTCTGGCCC

TCAACCTCAT CTTGATGGCA GCCTCTGGTG CTGTGTGCGA

AGTGAAGGAC GTTTGTGTTG GAAGCCCTGG TATCCCCGGC

ACTCCTGGAT CCCACGGCCT GCCAGGCAGG GACGGGAGAG

ATGGTCTCAA AGGAGACCCT GGCCCTCCAG GCCCCATGGG

TCCACCTGGA GAAATGCCAT GTCCTCCTGG AAATGATGGG

CTGCCTGGAG CCCCTGGTAT CCCTGGAGAG TGTGGAGAGA

AGGGGGAGCC TGGCGAGAGG GGCCCTCCAG GGCTTCCAGC

TCATCTAGAT GAGGAGCTCC AAGCCACACT CCACGACTTT

AGACATCAAA TCCTGCAGAC AAGGGGAGCC CTCAGTCTGC

AGGGCTCCAT AATGACAGTA GGAGAGAAGG TCTTCTCCAG

CAATGGGCAG TCCATCACTT TTGATGCCAT TCAGGAGGCA

TGTGCCAGAG CAGGCGGCCG CATTGCTGTC CCAAGGAATC

CAGAGGAAAA TGAGGCCATT GCAAGCTTCG TGAAGAAGTA

CAACACATAT GCCTATGTAG GCCTGACTGA GGGTCCCAGC

CCTGGAGACT TCCGCTACTC AGACGGGACC CCTGTAAACT

ACACCAACTG GTACCGAGGG GAGCCCGCAG GTCGGGGAAA

AGAGCAGTGT GTGGAGATGT ACACAGATGG GCAGTGGAAT

GACAGGAACT GCCTGTACTC CCGACTGACC ATCTGTGAGT

TCTGAGAGGC ATTTAGGCCA TGGGACAGGG AGGACGCTCT

CTGGCCTTCG GCCTCCATCC TGAGGCTCCA CTTGGTCTGT

GAGATGCTAG AACTCCCTTT CAACAGAATT CACTTGTGGC

TATTGGGACT GGAGGCACCC TTAGCCACTT CATTCCTCTG

ATGGGCCCTG ACTCTTCCCC ATAATCACTG ACCAGCCTTG

ACACTCCCCT TGCAAACTCT CCCAGCACTG CACCCCAGGC

AGCCACTCTT AGCCTTGGCC TTCGACATGA GATGGAGCCC

-continued

```
TCCTTATTCC CCATCTGGTC CAGTTCCTTC ACTTACAGAT

GGCAGCAGTG AGGTCTTGGG GTAGAAGGAC CCTCCAAAGT

CACACAAAGT GCCTGCCTCC TGGTCCCCTC AGCTCTCTCT

CTGCAACCCA GTGCCATCAG GATGAGCAAT CCTGGCCAAG

CATAATGACA GAGAGAGGCA GACTTCGGGG AAGCCCTGAC

TGTGCAGAGC TAAGGACACA GTGGAGATTC TCTGGCACTC

TGAGGTCTCT GTGGCAGGCC TGGTCAGGCT CTCCATGAGG

TTAGAAGGCC AGGTAGTGTT CCAGCAGGGT GGTGGCCAAG

CCAACCCCAT GATTGATGTG TACGATTCAC TCCTTTGAGT

CTTTGAATGG CAACTCAGCC CCCTGACCTG AAGACAGCCA

GCCTAGGCCT CTAGGGTGAC CTAGAGCCGC CTTCAGATGT

GACCCGAGTA ACTTTCAACT GATGAACAAA TCTGCACCCT

ACTTCAGATT TCAGTGGGCA TTCACACCAC CCCCCACACC

ACTGGCTCTG CTTTCTCCTT TCATTAATCC ATTCACCCAG

ATATTTCATT AAAATTATCA CGTGCCAGGT CTTAGGATAT

GTCGTGGGGT GGGCAAGGTA ATCAGTGACA GTTGAAGATT

TTTTTTTCCC AGAGCTTATG TCTTCATCTG TGAAATGGGA

ATAAGATACT TGTTGCTGTC ACAGTTATTA CCATCCCCCC

AGCTACCAAA ATTACTACCA GAACTGTTAC TATACACAGA

GGCTATTGAC TGAGCACCTA TCATTTGCCA AGAACCTTGA

CAAGCACTTC TAATACAGCA TATTATGTAC TATTCAATCT

TTACACAATG TCACGGGACC AGTATTGTTT CCTCATTTTT

TATAAGGACA CTGAAGCTTG GAGGAGTTAA ATGTTTTGAG

TATTATTCCA GAGAGCAAGT GGCAGAGGCT GGATCCAAAC

CCATCTTCCT GGACCTGAAG CTTATGCTTC CAGCCACCCC

ACTCCTGAGC TGAATAAAGA TGATTTAAGC TTAATAAATC

GTGAATGTGT TCACAAAAAA AAAAAAAAA
```

The present invention provides a SP-A polypeptide, variant, homologue, fragment or derivative for use for use in treatment and/or prevention of a parasitic infection in a subject.

Mannan-binding lectin (MBL) is a lectin that has an important role in innate immunity. MBL has an oligomeric structure (400-700 kDa), built of subunits that contain three peptide chains of about 30 kDa each.

MBL belongs to the class of collectins in the C-type lectin superfamily, whose function relates to pattern recognition in the first line of defense in the pre-immune host. MBL recognizes carbohydrate patterns, found on the surface of a large number of pathogenic micro-organisms, including bacteria, viruses, protozoa and fungi. Binding of MBL to a micro-organism results in activation of the lectin pathway of the complement system.

A MBL, variant, homologue, fragment or derivative for use according to the present invention may be a human SP-A having the GenBank accession number NM_00242 or MP_000233, as applicable. The variant, homologue, fragment or derivative may be as defined herein for SP-D.

The amino acid and nucleic acid sequences of such a human MBL are shown in SEQ ID NO: 10 and SEQ ID NO: 11 respectively.

```
                                    SEQ ID NO: 10
MSLFPSLPLLLLSMVAASYSETVTCEDAQKTCPAVIACSSPGINGFPGKD

GRDGTKGEKGEPGQGLRGLQGPPGKLGPPGNPGPSGSPGPKGQKGDPGKS

PDGDSSLAASERKALQTEMARIKKWLTESLGKQVGNKFFLTNGEIMTFEK

VKALCVKFQASVATPRNAAENGAIQNLIKEEAPLGIIDEKTEGQFVDLTG

NRLTYTNWNEGEPNNAGSDEDCVLLLKNGQWNDVPCSTSHLAVCEFPI
```

The amino acid sequence of MBL may be lacking the signal sequence (e.g. the amino acid sequence may lack residues 1 to 20 of SEQ ID NO: 10.

```
                                    SEQ ID NO: 11
GGTAAATATG TGTTCATTAA CTGAGATTAA CCTTCCCTGA

GTTTTCTCAC ACCAAGGTGA GGACCATGTC CCTGTTTCCA

TCACTCCCTC TCCTTCTCCT GAGTATGGTG GCAGCGTCTT

ACTCAGAAAC TGTGACCTGT GAGGATGCCC AAAAGACCTG

CCCTGCAGTG ATTGCCTGTA GCTCTCCAGG CATCAACGGC

TTCCCAGGCA AAGATGGGCG TGATGGCACC AAGGGAGAAA

AGGGGGAACC AGGCCAAGGG CTCAGAGGCT TACAGGGCCC

CCCTGGAAAG TTGGGGCCTC CAGGAAATCC AGGGCCTTCT

GGGTCACCAG GACCAAAGGG CCAAAAAGGA GACCCTGGAA

AAAGTCCGGA TGGTGATAGT AGCCTGGCTG CCTCAGAAAG

AAAAGCTCTG CAAACAGAAA TGGCACGTAT CAAAAAGTGG

CTCACCTTCT CTCTGGGCAA ACAAGTTGGG AACAAGTTCT

TCCTGACCAA TGGTGAAATA ATGACCTTTG AAAAAGTGAA

GGCCTTGTGT GTCAAGTTCC AGGCCTCTGT GGCCACCCCC

AGGAATGCTG CAGAGAATGG AGCCATTCAG AATCTCATCA

AGGAGGAAGC CTTCCTGGGC ATCACTGATG AGAAGACAGA

AGGGCAGTTT GTGGATCTGA CAGGAAATAG ACTGACCTAC

ACAAACTGGA ACGAGGGTGA ACCCAACAAT GCTGGTTCTG

ATGAAGATTG TGTATTGCTA CTGAAAAATG GCCAGTGGAA

TGACGTCCCC TGCTCCACCT CCCATCTGGC CGTCTGTGAG

TTCCCTATCT GAAGGGTCAT ATCACTCAGG CCCTCCTTGT

CTTTTTACTG CAACCCACAG GCCCACAGTA TGCTTGAAAA

GATAAATTAT ATCAATTTCC TCATATCCAG TATTGTTCCT

TTTGTGGGCA ATCACTAAAA ATGATCACTA ACAGCACCAA

CAAAGCAATA ATAGTAGTAG TAGTAGTTAG CAGCAGCAGT

AGTAGTCATG CTAATTATAT AATATTTTTA ATATATACTA

TGAGGCCCTA TCTTTTGCAT CCTACATTAA TTATCTAGTT

TAATTAATCT GTAATGCTTT CGATAGTGTT AACTTGCTGC

AGTATGAAAA TAAGACGGAT TTATTTTTCC ATTTACAACA

AACACCTGTG CTCTGTTGAG CCTTCCTTTC TGTTTGGGTA

GAGGGCTCCC CTAATGACAT CACCACAGTT TAATACCACA

GCTTTTTACC AAGTTTCAGG TATTAAGAAA ATCTATTTTG
```

```
TAACTTTCTC TATGAACTCT GTTTTCTTTC TAATGAGATA
TTAAACCATG TAAAGAACAT AAATAACAAA TCTCAAGCAA
ACAGCTTCAC AAATTCTCAC ACACATACAT ACCTATATAC
TCACTTTCTA GATTAAGATA TGGGACATTT TTGACTCCCT
AGAAGCCCCG TTATAACTCC TCCTAGTACT AACTCCTAGG
AAAATACTAT TCTGACCTCC ATGACTGCAC AGTAATTTCG
TCTGTTTATA AACATTGTAT AGTTGGAATC ATATTGTGTG
TAATGTTGTA TGTCTTGTTT ACTCAGAATT AAGTCTGTGA
GATTCATTCA TGTCATGTGT ACAAAGTTT CATCCTTTTC
ATTGCCATGT AGGGTTCCCT TATATTAATA TTCCTCAGTT
CATCCATTCT ATTGTTAATA GGCACTTAAG TGGCTTCCAA
TTTTTGGCCA TGAGGAAGAG AACCCACGAA CATTCCTGGA
CTTGTCTTTT GGTGGACATG GTGCACTAAT TTCACTACCT
ATCCAGGAGT GGAACTGGTA GAGGATGAGG AAAGCATGTA
TTCAGCTTTA GTAGATATTA CCAGTTTTCC TAAGTGATTG
TATGAATTTA TGCTCCTACC GGCAATGTGT GGCAGTCCTA
GATGCTCTAT GTGCTTGTAA AAAGTCAATG TTTTCAGTTC
TCTTGATTTT CATTATTCCT GTGGATGTAA AGTGATATTT
CCCCATGGTT TTAATCTGTA TTTCCCCAAC ATGTAATAAG
GTTGAACACT TTTTTATATG CTTATTGGGC ACTTGGGTAT
CTTCTTTTGT GAAGTACCCG TTCACATTTT TGTATTTTGT
TTAAATTAGT TAGCCAATAT TTTTCTTACT GATTTTTAAG
TTATTTTTAC ATTCTGAATA TGTCCTTTTT AATGTGTATT
ACAAATATTT TGCTAGTTTT TGACTTGCTC CTAATGTTGA
ATTTTGATGA ACAAAATTTC CTAATTTTGA GAAAGTCTTA
TTTATTCATA TTTTCTTTCA AAATTAGTGC TTTTTGTGTC
ATGTTTAAGA AATTTTTGCC CATCCCAAAA TCATAAGATA
TTTTTCATGA TTTTGAAACC ATGAAGAGAT TTTTCATGAT
TTTGAAATCA TGAAGATATT TTTCCATTTT TTTCTAATAG
TTTTATTAAT AAACATTCTA TCTATTCCTG GTAGAATAGA
TATCCACTTG AGACAGCACT ATGTAGGAAA GACCATTTTT
CCTCCACTGA ACTAGGGTGG TGCATTTTTG TAAGTTAGGT
AACTGTATGT GTGTGTGTCT GTTTCTGGGC TGTCTATTCT
AGTCTATTTG TTGATGCTTG TGTCAAACAG TACACTATCT
TAATTATTGT ACATTTATAG TTGTAACTAT AGTCCAGCTT
TGTTCTTCTT AAAGTCAAGA TTTCCATATA AATATTAGAA
ACAGCTTCTC AATTTCTACA AAATCCTGAT GAGGTTTCTA
CTGGGACCAC ATTGAGTCTA TCAATCAACT TATGCAGAAC
TGGCAACTTA CTACTGAATC TCTAATCAAT GTTCATCATG
TATCGCTTCA TGTAACTAGA ATTTCTTTAA CTTAATTGCT
ATGTTTTGAC ATTTTTAGTT TAAAAACCTT GTATATCTTG
TTTTGGTGGT TTTAGTGATT TTAATAATAT ATTTTAAATA
TTTTTTCTTT TCTATTGTTG TACACAGAAA TACAGTTAAG
TTTTGTGTGT AGTCTTACGA TGTTTAGTAA ACTCAATAAG
TTTATTTCTT AAATCTAGTA ATTTGTAGAT TCCTCTGGAT
TTTGTATATG CATAGTCATG TAAGCTGAAA ATATGGCAAT
ACTTGCTTCT TCCCAATTGC TTTACCTTTT TTCTTACCTT
ATTGCACTGG TTAGCAACCC CAATACAGAG ACCACCAGAT
CAGGTATAGA CTCCTGAAAG ACAATATAAT CAAGTGCTCC
AGTCAGGCCT ATCTAAACTG GATTCACAGC TCTGTCACTT
AATTGCTACA TGATCTAGAG CCAGTTACTT TGTGTTTCAG
CCATGTATTT GCAGCTGAGA GAAAATAATC ATTCTTATTT
CATGAAAATT GTGGGGATGA TGAAATAAGT TAACACCTTT
AAAGTGTGTA GTAAAGTATC AGGATACTAT ATTTTAGGTC
TTAATACACA CAGTTATGCC GCTAGATACA TGCTTTTTAA
TGAGATAATG TGATATTATA CATAACACAT ATCGATTTTT
AAAAATTAAA TCAACCTTGC TTTGATGGAA TAAACTCCAT
TTAGTCACA
```

The present invention provides a MBL polypeptide, variant, homologue, fragment or derivative for use for use in treatment and/or prevention of a parasitic infection in a subject.

Nucleic Acid

In another aspect the present invention provides a nucleic acid encoding for a SP-D polypeptide, or fragment thereof, for use according to the present invention.

The nucleic acid sequence may be or comprise the sequence shown as SEQ ID NO: 2.

The nucleic acid sequence may be or comprise the sequence shown as SEQ ID NO: 4.

Preferably, the SP-D nucleic acid is derived from a natural SP-D sequence, for example, the human SP-D sequence shown in SEQ ID NO: 2. The SP-D nucleic acid may lack sequence encoding the N-terminal domain and/or the collagen domain, preferably both. The SP-D nucleic acid may be a recombinant fragment of a natural SP-D nucleic acid sequence, preferably human SP-D depicted in SEQ ID NO: 2, which lacks substantially lacks residues 1-594, or any fragment, homologue, variant or derivative thereof. The SP-D nucleic acid may be a recombinant fragment of a natural SP-D nucleic acid sequence, preferably human SP-D sequence shown in SEQ ID NO: 2, comprising substantially residues 595-1128. Fragments, homologues, variants and derivatives of each of the above sequences are also included.

A triplet encoding the proline residue corresponding to position 200 of the human SP-D sequence (SEQ ID NO: 1) may be replaced by a codon encoding another residue. Preferably, the proline residue is replaced with an uncharged polar residue, for example, a cysteine, serine, threonine or methionine residue. The proline residue may be replaced with a serine residue. Thus, preferably the SP-D nucleic acid may comprise a codon encoding serine at position 598 to 560 of the human SP-D sequence shown in SEQ ID NO: 2. Such a replacement codon may therefore include AGC, AGT, TCA, TCC, TCG and TCT. The replacement codon may comprise AGC.

An SP-D nucleic acid may encode the rfhSP-D polypeptide having the sequence shown in SEQ ID NO: 3. The SP-D nucleic acid may comprise a sequence as set out in SEQ ID NO: 4 or may consists of a sequence as set out in SEQ ID NO: 4.

(Nucleic acid encoding rfhSP-D)

SEQ ID NO: 4
GGAAGCCCGGGATTGAAGGGGGACAAAGGCATTCCTGGAGACAAAGGAGC

AAAGGGAGAAAGTGGGCTTCCAGATGTTGCTTCTCTGAGGCAGCAGGTTG

AGGCCTTACAGGGACAAGTACAGCACCTCCAGGCTGCTTTCTCTCAGTAT

AAGAAAGTTGAGCTCTTCCCAAATGGCCAAAGTGTGGGGGAGAAGATTTT

CAAGACAGCAGGCTTTGTAAAACCATTTACGGAGGCACAGCTGCTGTGCA

CACAGGCTGGTGGACAGTTGGCCTCTCCACGCTCTGCCGCTGAGAATGCC

GCCTTGCAACAGCTGGTCGTAGCTAAGAACGAGGCTGCTTTCCTGAGCAT

GACTGATTCCAAGACAGAGGGCAAGTTCACCTACCCCACAGGAGAGTCCC

TGGTCTATTCCAACTGGGCCCCAGGGGAGCCCAACGATGATGGCGGGTCA

GAGGACTGTGTGGAGATCTTCACCAATGGCAAGTGGAATGACAGGGCTTG

TGGAGAAAAGCGTCTTGTGGTCTGCGAGTTCTGA

As used herein, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

SP-D nucleic acids, variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence. Preferably said variant, homologues or derivatives code for a polypeptide having biological activity.

As indicated above, with respect to sequence homology, preferably there is at least 50 or 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The nucleic acid sequence may have at least 80, 85, 90, 95, 98 or 99% identity to the sequence shown as SEQ ID No. 2, or 4, provided that it encodes a SP-D polypeptide suitable for use as defined in the first aspect of the invention.

The SP-D nucleic acid for use according to the present invention may be in the form of a vector which comprises a nucleic acid sequence as defined above. Such a vector may be used to introduce the nucleic acid sequence into a host cell so that it expresses and produces a peptide suitable for use according to the first aspect of the invention.

The vector may, for example, be a plasmid or a viral vector, such as a retroviral vector or a lentiviral vector.

The vector may be capable of transfecting or transducing a lung cell, for example an ATII cell, a sub mucosal cell or a Clara cell.

Alternative Activated Macrophages

The present inventors have also shown that SP-D is able to enhance alternative activation of alveolar macrophages (AAM). This is associated with protection against parasite infection and decreased parasite burden.

Macrophages are involved in both innate and adaptive immune responses. Depending on the types of cytokines that macrophages are exposed to, these cells are subjected to classical (Th1) or alternative (Th2) activation. In the first case, macrophages, particularly when activated by interferon gamma (IFN-α) or by lipopolysaccharide (LPS), have the capacity, through the production of NO and other intermediates, to destroy the remaining microorganisms in the inflammatory loci. In the second case, after exposure to cytokines such as IL-4, IL-10, or IL-13, macrophages produce polyamines and proline, which induce proliferation and collagen production, respectively. Thus AAMs are well-known in the art. A non-exhaustive, illustrative list of markers for AAMs known in the art includes CCL18, CCL22, ECF-L/YM1, Stabilin-1 and RELMα. The ability of SP-D, or a fragment thereof, to induce or increase alternative activation of macrophages may therefore be assessed using techniques known in the art such as flow cytometry or fluorescent microscopy to determine the level of such markers. An increase in the detection of such markers in the presence of SP-D, compared to the level of detection under control conditions (absence of SP-D), indicates an ability to induce or increase alternative activation of macropahges.

As used herein, 'enhancing alternative activation of alveolar macrophages' refers to increasing the level of activation of AAM (i.e. by increasing the level of AAM activation markers, such as YM1 and RELMα as detailed in the Examples section) or to increasing the number of AAM.

The SP-D, or fragment, variant, homologue or derivative thereof, for use according to the present invention may induce or increase alternative activation of macrophages.

Innate Lymphoid Type 2 Cells

Innate lymphoid type 2 cells (ILC2) are newly identified innate cells that have a crucial role in protection against helminth infections by inducing IL-13 cytokine responses. ILC2s may be identified by the expression of CD127, SCA-1, T1/ST2 and ICOS, as is detailed in the Examples section provided herein. Alternative markers for ILC2s may also be available, as provided in the art.

The present inventors have surprisingly found that administration of SP-D to a subject increases the number of ILC2 cells in the lungs. As used herein 'increases the number' is synonymous with 'induce', 'enhance' or 'stimulate'. Each of these terms refers to the fact that the number of ILC2 cells is greater in a subject following administration of SP-D.

The induction of ILC2s by SP-D may be assessed using techniques well known in the art, for example using flow cytometry or fluorescent microscopy to assay the level of ILC2 markers as described above.

Opsonisation

The present inventors have surprisingly shown that SP-D is able to bind to parasites associated with the lung and act as an opsonin.

As used herein, opsonin is used according to its standard meaning to refer to a molecule that enhances phagocytosis by marking an antigen for an immune response. As such the SP-D, or fragment thereof, for use according to the present invention may act as an opsonin of the parasite.

Methods for measuring phagocytosis are well known in the art. A non-exhaustive, illustrative summary is provided in Chow et al. (2004; Measurements of Phagocytosis and Phagosomal Maturation; Current Protocols in Cell Biology; 22:15.7.1-15.7.33).

The SP-D for use according to the present invention may opsonise a parasitic nematode during the lung-associated stage of development, typically the L4 stage.

Parasitic Infection

As used herein the term 'parasitic infection' relates to a condition caused by a protozoa or helminth. Specifically the term 'parasitic infection' relates to an infection caused by an endoparasite.

Parasites normally enter the body through the skin or mouth and are usually contracted from contaminated food or water, bug bites or sexual contact.

Symptoms of parasitic infection vary depending on the specific parasite. The symptoms may not be obvious and may mimic anemia or a hormone deficiency. Some of the potential symptoms can include itching, abdominal pain, weight loss, increased appetite, bowel obstructions, diarrhoea and vomiting eventually leading to dehydration, sleeping problems, worms present in the vomit or stools, anemia, aching muscles or joints, general malaise, allergies, fatigue or nervousness.

SP-D for use according to the present invention may be for use in treating and/or preventing a parasite infection, wherein the lifecycle of the parasite includes infestation of the host lung.

As used herein, 'infestation of the host lung' means that at least one stage of the lifecycle of the parasite occurs in the lung of the host. The parasite may be present in the lung of the host at a stage, or multiple stages, during its development, or the mature parasite may localise to the lung of the host.

Parasitic infections affecting the lung may be caused by protozoa, nematodes and trematodes. The diseases may be grouped according to their manner of presentation as follows: (1) those presenting with focal lesions and (2) those which characteristically present with diffuse lung disease. Focal lung lesions may be divided into cystic lung lesions, coin lesions and consolidation/pleural effusion. Diffuse lung disease may be divided into transient pulmonary infiltrates and alveolar/interstitial lung changes.

A non-exhaustive, illustrative list of parasites with a lifecycle which involves infestation of the lung is provided below.

Hydatidosis (Hydatid disease) is caused by larvae of *Echinococcus* tapeworm species, the definite hosts of which are members of the Canidae family. Most cases are caused by *Echinococcus granulosus*. When humans become accidental intermediate hosts after eating food contaminated with eggs, the ingested eggs hatch, releasing larvae which migrate from the gastrointestinal tract to the circulation. The eggs travel to the liver or lungs and slowly develop into hydatid cysts over a period of several months or years. Occasionally, lung cysts form after transdiaphragmatic spread of parasites following the rupture of liver cysts.

Dirofilariasis is caused by the dog heartworm *Dirofilaria immitis*. Adult worms live in the right ventricle of the definitive canine hosts and produce circulating microfilaria which can be transmitted by a variety of mosquito species to humans. In humans the worms pass through the right ventricle but fail to mature and are swept away to peripheral pulmonary arteries.

Paragonimiasis is caused by lung flukes of the genus *Paragonimus*. *Paragonimus westermani* is responsible for most cases. The adult worms are found in pulmonary cysts, usually in pairs. They mature in a fibrous host-derived capsule, usually in the upper zones of the lung.

Amoebiasis is caused by the protozoan, *Entamoeba histolytica*. The motile trophozoite forms of the parasite live in the lumen of the large intestine where they multiply and differentiate into the cyst forms. Amoebic pleuropulmonary disease is the most common complication of amoebic liver abscess, occurring in 15% of patients with amoebic liver disease. It most commonly occurs by direct extension from a superior right lobe hepatic abscess through the diaphragm into the right lower lobe of the lung, presenting with cough, pleuritic pain and dyspnoea Ascariasis is caused by *Ascaris lumbricoides*. Transmission of the disease is faecal-oral. After eggs are ingested they hatch and larvae migrate via the portal circulation to the liver then via the heart to reach the lungs. Larvae then ascend to the trachea, are swallowed and eventually develop into adults in the small intestine, producing eggs 10-12 weeks after ingestion.

Ancylostomiasis is caused by two species of hookworm, *Ancylostoma duodenale* and *Necator americanushe*. Larvae penetrate blood vessels and undergo heart-lung migration before breaking out into the alveoli and ascending to the pharynx from where they are swallowed.

Schistosomiasis is most commonly caused by three main species of schistosomes: *Schistosoma mansoni, Schistosoma haematobium* and *Schistosoma japonicum*. Humans are infected by cercariae during contact with fresh water. The organisms enter the circulation and pass through the heart, lungs and then the liver to reach the target venous plexus. In severe longstanding *S. mansoni* and *S. japonicum* infections, the development of hepatosplenomegaly and portal hypertension may lead to diversion of eggs to the lung vasculature. This results in obliterative arteritis which may cause pulmonary hypertension.

Strongyloidiasis is caused by the nematode *Strongyloides stercoralis*. Filariform larvae penetrate the skin, enter blood vessels and undergo heart and lung migration. They migrate into alveoli and subsequently ascend to the trachea. Larvae are swallowed and develop in the small intestine into adult worms which produce eggs.

A variety of anti-parasite therapies are known in the art. A non-exhaustive, illustrative list of such therapies is provided below.

Antinematode therapies include mebendazole, pyrantel pamoate, thiabendazole, diethylcarbamazine and ivermectin.

Anticestode therapies include niclosamide, praziquantel and albendazole.

Antitrematode therapies include praziquante.

Antiamoebic therapies include rifampin and amphotericin B.

Antiprotozoal therapies include melarsoprol, eflornithine, metronidazole, tinidazole and miltefosine.

The use of SP-D according to the first aspect of the present invention may include administration of the SP-D in combination with an anti-parasitic therapy.

Helminths Infection

The parasitic infection may be a helminths infection.

Helminths are worm-like organisms that live in and feed on living hosts, receiving nourishment and protection while disrupting their hosts' nutrient adsorption, causing weakness and disease.

Helminths are a polyphyletic group of morphologically similar organisms, consisting of members of the following taxa: cestodes (tapeworms), nematodes (roundworms) and trematodes (flukes).

Cestodes (tapeworms) typically live in the digestive tracts of vertebrates as adults, and often in the bodies of other species of as juveniles. Over a thousand species have been described and all vertebrate species may be parasitized by at least one species of tapeworm. Examples of parasitic cestode species include *Taenia solium, T. saginata, Diphyllobothrium* spp., *Hymenolepis* spp. and *Echinococcus* spp.

Trematodes (flukes) are internal parasites of molluscs and vertebrates. Most trematodes have a complex lifecycle with at least two hosts. The primary host, where the flukes sexually reproduce, is a vertebrate. The intermediate host, which is the agent of dispersal, is usual a snail.

Trematodes can be classified into two groups, on the basis of the system the infect in the vertebrate host.

Tissue trematodes infect the bile ducts, lungs or other tissues. This group includes the lung fluke, *Paragonimus westermani*, and the liver flukes, *Clonorchis sinensis* and *Fasciola hepatica*.

Blood trematodes inhabit the blood in some stages of their lifecycle. Blood flukes include species of the genus *Schistosoma*.

SP-D for use according to the present invention may be for use in treating and/or preventing a helminth infection, wherein the lifecycle of the helminth involves infestation of the host lung.

Parasitic Nematode Infection

The parasite infection to be prevented and/or treated according to the present invention may be a parasitic nematode infection.

The phylum Nematoda, also known as the roundworms, is the second largest phylum in the animal kingdom, encompassing up to 500,000 species. Members of Nematoda are elongated, with bilaterally symmetric bodies that contain an intestinal system and a large body cavity.

Gastrointestinal (GI) nematode infections are amongst the most prevalent infection of humans worldwide, with an estimated 3.5 billion cases of which 450 million individuals are seriously ill as a result.

Several clinical signs and symptoms can occur in patients with nematode infections. The specific symptoms may vary between patients and depend, at least in part, on the infecting species and the location of the invasion.

The life-cycles of the most common GI nematodes of humans are essentially similar, developing through L1-L4 larvae into mature L5 worms. In all, the adult worms reproduce sexually and the mature female worms produce and release eggs into their immediate environment of the host intestine. These eggs pass into the external environment via host faeces and then the L1 (first larval stage) develop within the eggs. The larvae most commonly develop through two moults within the external environment until they reach infective L3. Transmission to a host may occur by ingestion of infective eggs, ingestion of infective larval stages or penetration of the skin by infective larval stages. The extent of development in the external environment and mode of transmission to a host varies between species.

Infective L3 migrate through tissues or blood, depending on the infecting species, to the lungs of the host where L4 larvae commonly develop. Depending on the particular nematode species; L3, L4 or young adult worms then migrate up the trachea and are swallowed so as to enter the intestine. Development to mature worms then occurs in the intestine.

Intestinal invasion may be asymptomatic when the burden of worms is low, however, such invasion may result in presentations such as abdominal pain (usually vague), abdominal cramps/colic, diarrhoea, vomiting and constipation.

Lung invasion by nematode larvae may be associated with fever, cough, blood-tinged sputum, wheezing, rales, dyspnea, substernal pain, pulmonary consolidations, eosinophilia, urticarial, asthma and angioneurotic oedema.

Invasion of muscle and other tissues (depending on the specific species infecting) may be associated with myalgias, fever, oedema, spasm, periorbital and facial edema, photophobia, sweating, conjunctivitis, weakness or prostration, pain upon swallowing, subconjunctival, retinal and ungual hemorrhages, rashes and formication, encephalitis, myocarditis, nephritis, pneumonia, meningitis and neuropathy.

SP-D may be used according to the present invention in order to reduce the nematode burden in a subject and/or to reduce (lessen) at least one symptom which is associated with the disease caused by the infection, for example one of the symptoms provided above.

Human nematode infections are typically caused by nematodes belonging to the order of Spirurida, Strongylida, Ascaridida, Rhabditidia or Oxyurida. SP-D may be used according to the present invention in order to treat and/or prevent infection caused by a nematode belonging to one of these orders.

The major GI nematode parasites of humans are *Ancylostoma duodenale/Necator americanus, Ascaris lumbricoides, Trichuris trichiura, Enterobius vermicularis* and *Strongyloides stercoralis*. SP-D may be used according to the present invention in order to treat and/or prevent infection caused by one of these nematode species.

Parasitic nematode infections are also relevant for livestock. Nematodes are the principal internal parasites that plague grazing ruminants such as sheep and cattle and nematode infection is therefore a major concern for industries which involve the keeping of such livestock. Failure to control nematode infections can lead to general ill health of the animals and decreased productivity and yield.

A non-exhaustive, illustrative list of nematodes that infect cattle includes *Haemonchus placei, Ostertagia ostertagi, Ostertagia bisonis, Trichostrongylus axei, Nematodirus helvetianus, Cooperia* spp., *Bunostomum phlebotomum, Oesophagostomum radiatum, Trichuris discolor, Chabertia ovina* and *Capillaria bovis*.

A non-exhaustive, illustrative list of nematodes that infect small ruminants, such as sheep and goats, includes *Haemonchus placei, Marshallagia marshalli, Ostertagia* spp., *Trichostrongylus axei, Bunostomum trigonocephalum, Capillaria* spp., *Cooperia* spp., *Nematodirus* spp., *Strongyloides papillosus, Trichostrongylus colubriformis, Ascarus suum, Chabertia ovine, Trichuris* spp. and *Skrjabinema ovis*.

The intensive management approach of using anthelmintics to control nematode infection in livestock, combined with environmental factors and dosing practices, has resulted in the selection of parasites resistant to some classes of anthelmintic products. As such, an alternative strategy for the controlling nematode infections in livestock is required.

The present invention therefore provides SP-D for use in treating and/or preventing parasitic nematode infection in a subject. The subject may be a mammal, for example the subject may be a human.

The subject may also be a domesticated ruminant, for example sheep, goat or cattle.

The use of SP-D according to the present invention may reduce the parasite burden in a subject. Reduction of the parasite burden means that the number of nematode larvae and/or mature worms in the subject is less than it was prior to administration of SP-D and/or that the number of nematode larvae and/or mature worms is less than in an equivalent control subject which has not been administered SP-D.

Treatment and Prevention

SP-D is for use according to the present invention in order to treat or prevent infection by a parasite.

When used for the prevention of parasite infection, the invention relates to the prophylactic use of SP-D. In this aspect SP-D may be administered to a subject who has not yet contracted the infection and/or who is not showing any symptoms of disease associated with the infection to prevent or impair the cause of the infection or to reduce or prevent development of at least one symptom associated with the infection. The subject may have a predisposition for, or be thought to be at risk of developing, a parasitic infection.

When used for the treatment of parasitic infection, the invention relates to the therapeutic use of SP-D. Herein SP-D may be administered to a subject having an existing infection or condition in order to lessen, reduce or improve at least one symptom associated with the infection and/or to slow down, reduce or block the progression of the infection.

The symptom(s) of the parasitic infection may be a symptom as defined above.

The term 'treating', as used herein, relates to the therapeutic use of a therapeutic entity. As such the entity may be administered to a subject having an existing infection or condition in order to lessen, reduce or improve at least one symptom associated with the infection and/or to slow down, reduce or block the progression of the infection.

The term 'preventing', as used herein, relates to the prophylactic use of a therapeutic entity. The entity may be administered to a subject who has not yet contracted the infection and/or who is not showing any symptoms of disease to prevent or impair the cause of the infection or disease or to reduce or prevent development of at least one symptom associated with the infection or disease. The subject may have a predisposition for, or be thought to be at risk of developing, the infection or disease.

Anti-Nematode Therapies

The major means of controlling human GI nematode infections is the administration of chemotherapeutic anthelmintic drugs such as albendazole, mebendazole, thiabendazole, ivermectin, piperazine, pyrantel pamoate, and levamisole.

Benzimidazoles (e.g. albendazole, mebendazole and thiabendazole) are broad-spectrum drugs that bind to free b-tubulin, inhibiting its polymerisation and so interfering with microtubule-dependent glucose uptake by the parasite.

Imidazothiazoles/tetrahydropyrimidines (e.g. levamisole and pyrantel pamoate) stimulate the nicotinic acetylcholine receptors, resulting in overstimulation, blockade of the neuromuscular junctions and rigid paralysis of the nematodes. The nematodes are then unable to move in the intestinal tract and are swept out by the peristaltic action in the intestine.

Macrocyclic lactones (e.g. ivermectin) are generally used in the treatment of nematode infections in livestock, but are increasingly used for the treatment of human nematode infections. They act by opening glutamate-gated chloride channels, increasing chloride ion conductance, and leading to defects in neurotransmission and flaccid paralysis.

Heterocyclic ethyleneamines (e.g. piperzine) are used against a relatively small number of nematodes (e.g. *A. lumbriciodes* and *E. vermicularis*). It acts by reversibly inhibiting neuromuscular transmission by stimulating gamma-aminobutyric acid receptors in nematode muscle which results in flaccid paralysis.

SP-D for use according to the present invention may involve the administration of SP-D in combination with an anti-nematode therapy. For example the SP-D may be administered in combination with one of the entities detailed above.

As used herein, 'in combination' means that the SP-D and anti-nematode therapy may be used simultaneously, sequentially or separately.

As used herein, simultaneously refers to the situation wherein the SP-D and anti-nematode therapy are administered within 30 minutes of each other.

Herein the SP-D and anti-nematode therapy may be administered sequentially (i.e. administration of one followed within 12 hours, 24 hours, 48 hours, 1 week or 1 month by administration of the second). This process may be repeated for multiple doses of each.

Separate administration of SP-D may be performed before treatment with the anti-nematode therapy is commenced or after treatment with the anti-nematode therapy is completed.

Administration

The administration of SP-D can be accomplished using any of a variety of routes that make the active ingredient bioavailable. For example, the SP-D can be administered by oral and parenteral routes, intranasally, intraperitoneally, intravenously, subcutaneously, transcutaneously or intramuscularly.

Preferably, SP-D is administered such that it is available in an active form in the lungs of the subject to which it is administered.

For example, the SP-D may be administered intranasally or in the form of an aerosol.

Typically, a physician will determine the actual dosage that is most suitable for an individual subject and it will vary with the age, weight and response of the particular patient. The dosage is such that it is sufficient to reduce and/or prevent parasite infection.

The dosage is such that it is sufficient to stabilise or improve symptoms of the disease associated with parasitic nematode infection.

A pharmaceutical composition according to the present invention may be administered as described above.

Pharmaceutical Composition

The present invention also provides a pharmaceutical composition comprising SP-D for use in the treatment and/or prevention of parasitic infection.

The pharmaceutical composition comprises SP-D, or a fragment thereof, as defined above.

SP-D may be administered with a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

The present invention also provides a pharmaceutical composition comprising helminths for use in the prevention and/or treatment of allergy, inflammation or infection.

Administration of the composition results in increased levels of SP-D. In particular, administration of the composition results in increased levels of SP-D in the lung.

An 'increase in the level of SP-D in a subject' means that the amount of SP-D is greater following administration of the composition than it was prior to the administration.

The composition comprises whole helminths or a preparation thereof. A 'preparation thereof' refers to a processed form of the whole helminth, for example a homogenised preparation.

The helminth is as defined herein. For example the helminth may be a nematode, such as *N. brasiliensis*.

The inflammation may be lung inflammation.

The allergy and/or inflammation may be associated with asthma.

The infection may be, for example, a viral infection (e.g. Respiratory syncytial virus (RSV) or influenza) or a bacterial infection (e.g. tuberculosis).

The composition may comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

Kit

The present invention also provides a kit comprising SP-D for use in the treatment and/or prevention of a parasitic infection.

The kit comprises SP-D as defined above.

The kit may be in the form of pharmaceutical combination further comprising an anti-parasite therapy and/or pharmaceutical composition as defined above.

Method

The present invention further relates to a method for the treatment and/or prevention of a parasitic infection which comprises the step of administering SP-D to a subject.

The method comprises the use of SP-D as defined above.

The method may also comprise the use of an anti-parasite therapy and/or a pharmaceutical composition as defined above.

The present invention also relates to use of SP-D in the manufacture of a medicament for treating and/or preventing a parasitic infection in a subject.

The present invention also relates to a method for the treatment and/or prevention of allergy, inflammation or infection which comprises that step of administering a composition comprising helminths or a preparation thereof to the subject.

The helminth may be a helminth as defined herein. For example the helminth may be a nematode, such as *N. brasiliensis*.

Administration of the composition causes an increase in the levels of SP-D in the subject. In particular, administration of the composition results in increased levels of SP-D in the lung.

Administering the composition may enhance the alternative activation of alveolar macrophages in the subject.

The present invention also relates to a method for determining the presence of a parasitic infection in a subject comprising the step of determining the level of SP-D in a sample from the subject, wherein increased levels of SP-D compared to a control indicates parasitic infection.

The sample may be a bronchoalveolar lavage (BAL), sputum or blood sample. Preferably the sample is a BAL sample.

The level of SP-D in a sample may be determined by standard methods known in the art, for example ELISA, ELIspot, mass spectrometry or western blot.

The control may be the level of SP-D in an equivalent sample from a subject who is known not to be suffering from a parasitic infection. The control may be the level of SP-D derived as an average level in equivalent samples from a plurality of individuals who are known not to be suffering from a parasitic infection.

A level of SP-D in the subject sample of 2, 4, 10, 20, 50 or 100-fold greater than the control level may indicate the presence of a parasitic infection.

The method may be used to monitor the progression of a parasitic infection. That is, samples may be taken from a subject who is known to be suffering from a parasitic infection at temporal intervals in order to monitor changes in the level of SP-D. In this embodiment, the level of SP-D in the sample may be compared to a control as defined above and/or the level of SP-D in samples taken from the subject at earlier time-points. Herein, increased levels of SP-D compared to those determined in earlier samples indicates continued and/or progressive parasitic infection whilst decreased levels of SP-D compared to those determined in earlier samples may indicate reduced parasite burden and/or parasitic infection.

Increased SP-D levels compared to those determined in earlier samples may indicate the need to alter and/or increase the treatment administered to the subject in order to reduce parasite burden.

The parasitic infection is a parasitic infection as defined above.

Use

The present invention also provides the use of SP-D or a fragment, homologue, variant or derivative thereof in combination with helminth larva or a preparation thereof to enhance alternative activation of alveolar macrophages and/or to induce innate lymphoid type 2 cells.

The present invention also provides SP-D or a fragment, homologue, variant or derivative thereof in combination with helminth larva or a preparation thereof for use to enhance alternative activation of alveolar macrophages and/or to induce innate lymphoid type 2 cells.

Helminth larvae or a preparation refers to the larval stage of the parasite which develops or is localised to the lung of a subject. As such larva or a preparation thereof may refer to L1-L4 larvae. The stages of particular parasitic helminths which localise to the lungs are known in the art.

The helminth is a parasitic helminth as defined herein. For example the helminth may be a nematode, such as *N. brasiliensis*.

A 'preparation thereof' refers to a processed form of the helminth larva, for example a homogenised preparation.

In one embodiment, the helminth larva or a preparation thereof are coated with SP-D or a fragment, homologue, variant or derivative thereof.

The invention will now be further described by way of Examples, which are meant to serve to assist one of ordinary skill in the art in carrying out the invention and are not intended in any way to limit the scope of the invention.

EXAMPLES

Example 1

SP-D Levels are Increased Following *N. brasiliensis* (Nb) Infection

Analysis of SP-D levels in the BAL and serum of Nb infected mice showed SP-D levels to correlate with the kinetics of Nb infection (FIG. 1A). Highest levels of SP-D were found at the peak of infection; namely day 7 post primary infection in both BAL and serum. Following secondary infection, SP-D levels were also enhanced.

Example 2

SP-D Expression is Modulated by IL-4 and IL-13 Cytokine Levels

The inventors investigated requirements of IL-4 and IL-13 for SP-D production in response to Nb infection. Nb and IL-4/IL-13 double KO mice were exposed to primary (1°) and secondary (2°) Nb infection and at 5 days P.I, SP-D levels in BAL fluid and serum was quantified (FIG. 1B). WT mice had significantly higher SP-D levels compared to KO mice, thereby suggesting that SP-D production following infection was indeed dependent on IL-4 and IL-13.

Example 3

Intra-nasal Administration of SP-D Enhances Protective Immunity to Nb

Figure 2:
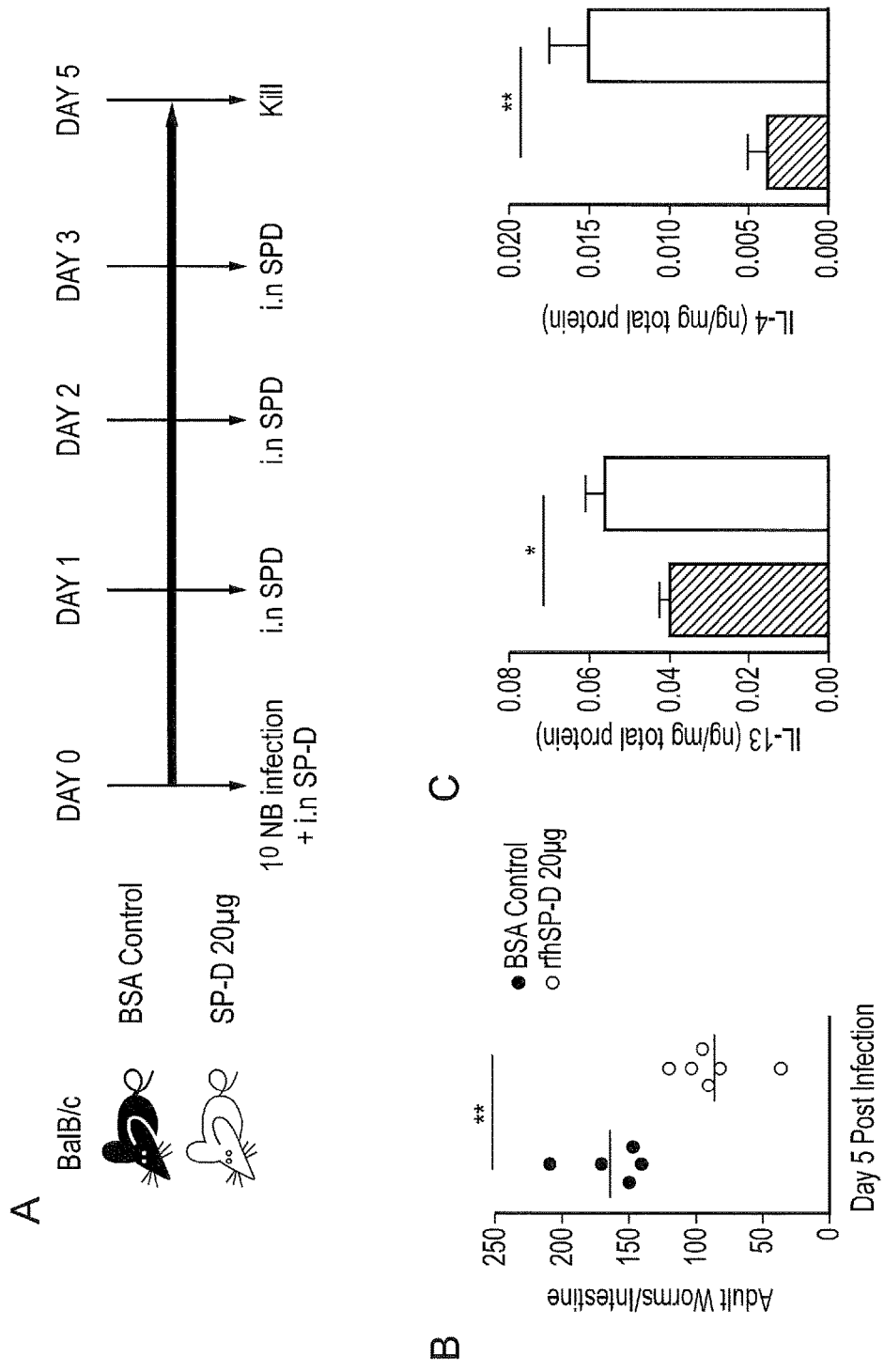
FIG. 2: Intra-nasal administration of SP-D enhances protection to Nb. (a) rfhSP-D treated or untreated mice were given Nb infection and killed at day 5 P.I. (b) Enhanced protection in rfhSP-D treated mice was established by quantification of intestinal worm burdens at day 5 P.I. (c) IL-4 and IL-13 cytokine levels in lung homogenates was detected by ELISA. (d) rfhSPD was incubated with 20 mM maltose to block the CRD head region before being intra-nasally administered. (e) Numbers of ILC2s and polarization of macrophages was also determined. Intestinal worm burden was quantified at day 5 P.I. Data are representative of two individual experiments. N=5-6 mice per group. *P<0.05, **P<0.01.
Figure 2:
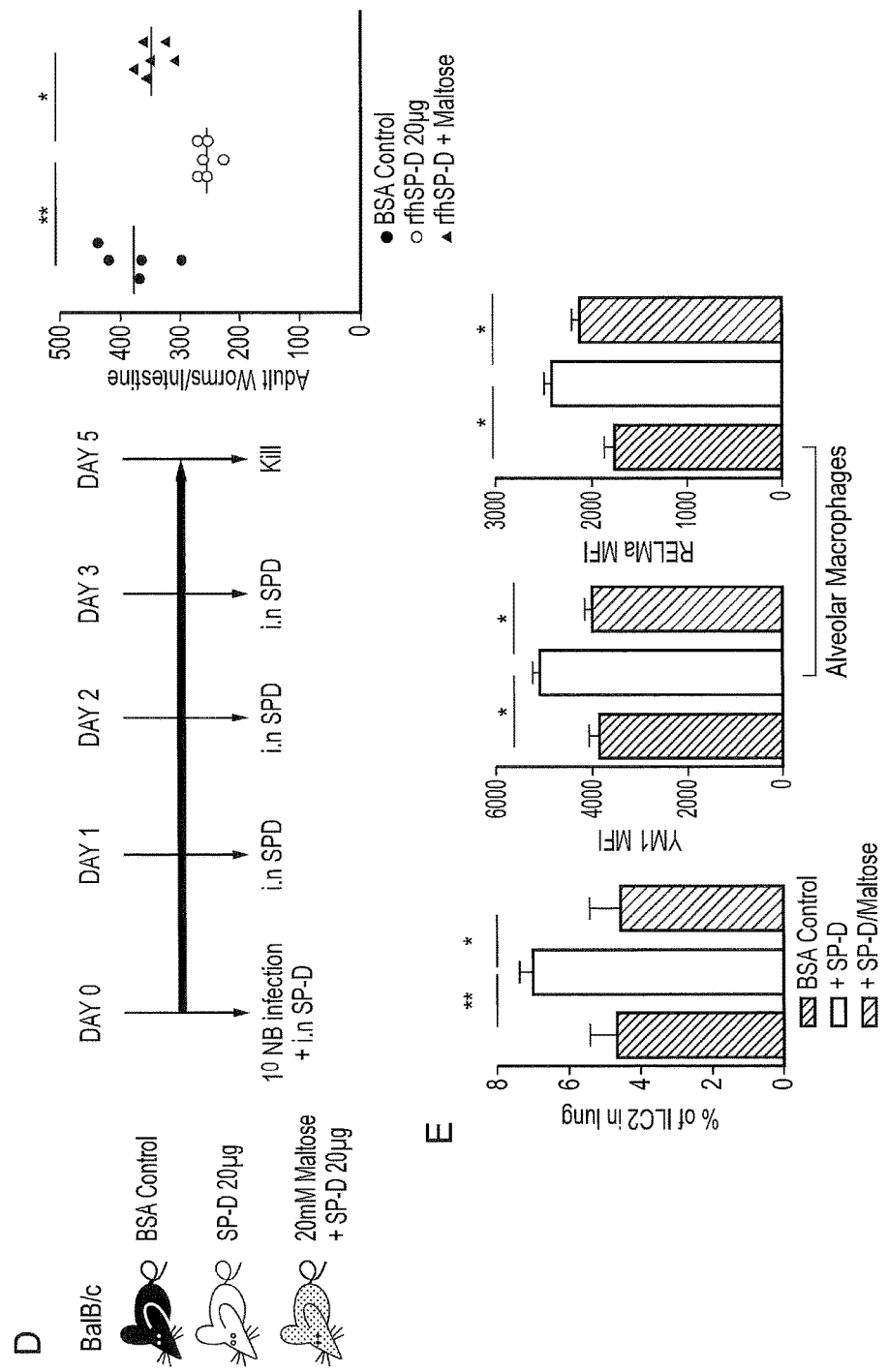

The inventors performed intra-nasal administration of rfhSP-D prior to Nb infection (FIG. 2A), This manipulation of pulmonary SP-D levels resulted in enhanced host ability to control infection as demonstrated by reduced intestinal burdens of adult Nb in rfhSP-D treated mice compared to BSA treated controls (FIG. 2B). Additionally, SP-D treated mice had significantly increased levels of Nb protective pulmonary TH2 cytokines IL-4 and IL-13 (FIG. 2C).

SP-D binds preferentially to inositol, maltose and glucose. Previous studies have shown the dependency of SP-D's function on its head region, which can bind directly to pathogens and mediate their clearance via opsonisation and neutralization. The inventors used 20 mM maltose to block CRD head region of rfhSPD. Mice treated with maltose-blocked SP-D had higher worm burdens than mice treated with rfhSPD alone (FIG. 2D).

Moreover, the higher worm burdens in mice treated with maltose-blocked SP-D Associated with reduced ILC2 induction and reduced polarization of macrophages to the alternatively activated phenotype when compared to mice treated with SP-D only (FIG. 2E).

Elevated pulmonary SP-D levels therefore enhances host ability to control Nb infection, this is related to SP-D associated enhancement in host TH2 immunity to Nb and ability of CRD domains to interact with ligands.

Example 4

Figure 3:
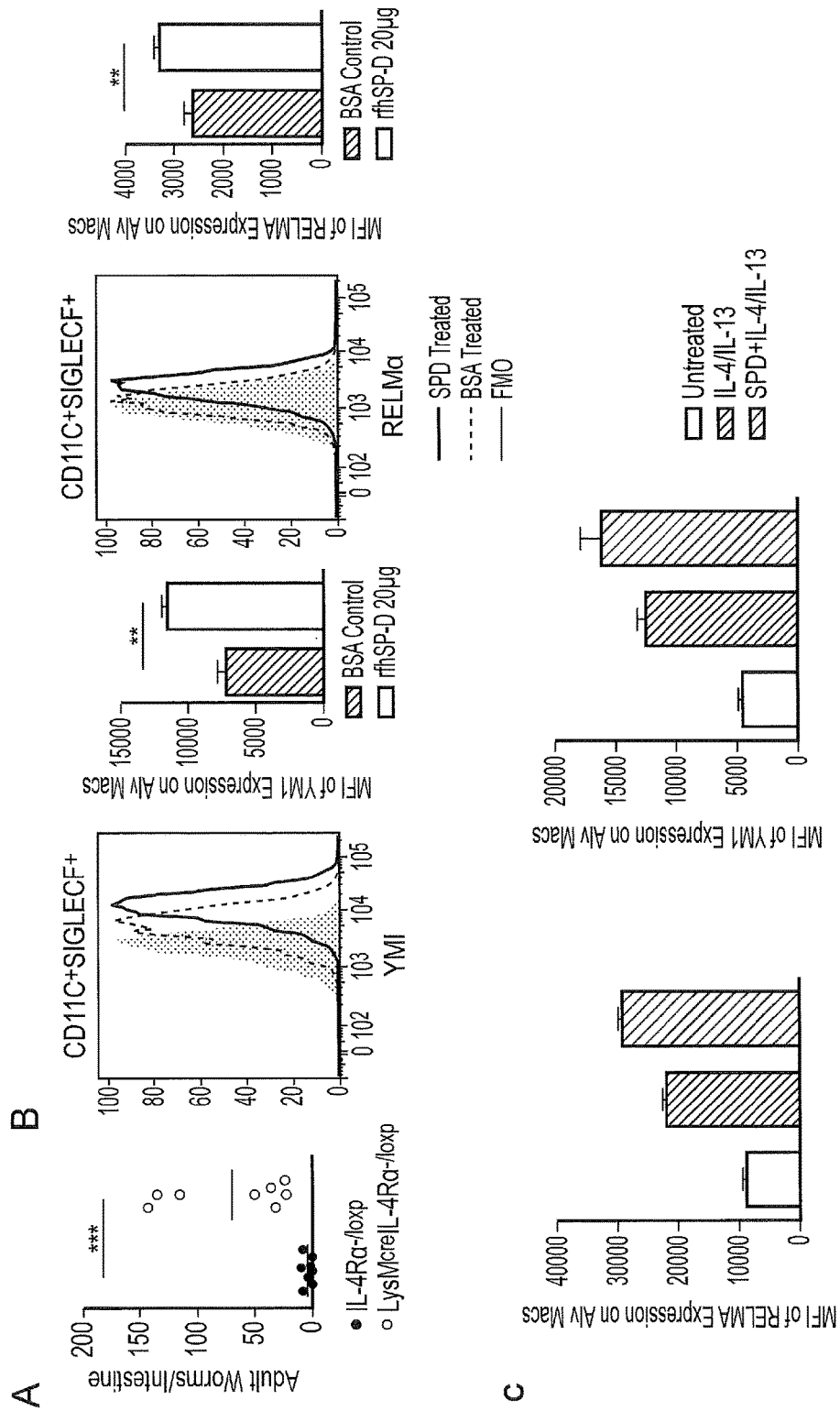
FIG. 3: SP-D enhances alternative activation of alveolar macrophages. (a) WT or LysM$^{cre}$IL-4Rα$^{-/lox}$ were given secondary Nb infection and at day 5 P.I. intestinal worm burdens were quantified. (b) MFI of YM1 and Relmα expression on CD11c$^+$SiglecF$^+$ alveolar macrophages from D5 post-infected rfhSP-D treated or untreated mice was established by FACS analysis. (c) Sorted macrophages from naïve lungs of mice were cultured for 60 hrs with either IL-4/IL-13, rfhSP-D+IL-4/IL-13 or left untreated before staining for Relmα and YM1. MFI was measured by flow cytometry. (d) Macrophages isolated from lungs of rfhSP-D treated or untreated mice were intra-nasally transferred into naïve BALB/c mice. Mice were thereafter infected with Nb and worm burdens were quantified at Day 5 P.I. (e) Flow cytometric analysis of cell suspension of whole lung stained for ILC2 (lin$^-$CD127$^+$IL33$^+$SCA-1$^+$ICOS$^+$) from rfhSP-D treated or untreated mice. Data are representative of one or two individual experiment. N=5-6 mice per group. P<0.01, *P<0.001.
Figure 3:
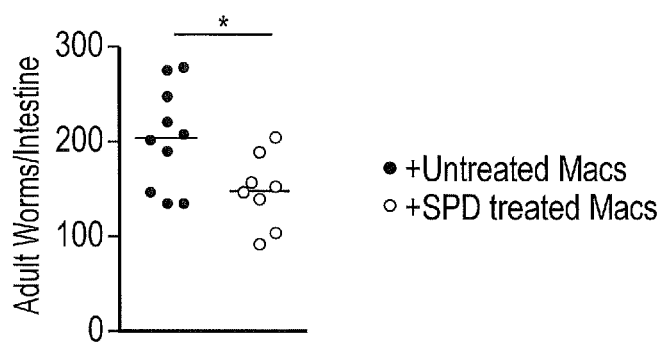
Figure 3:
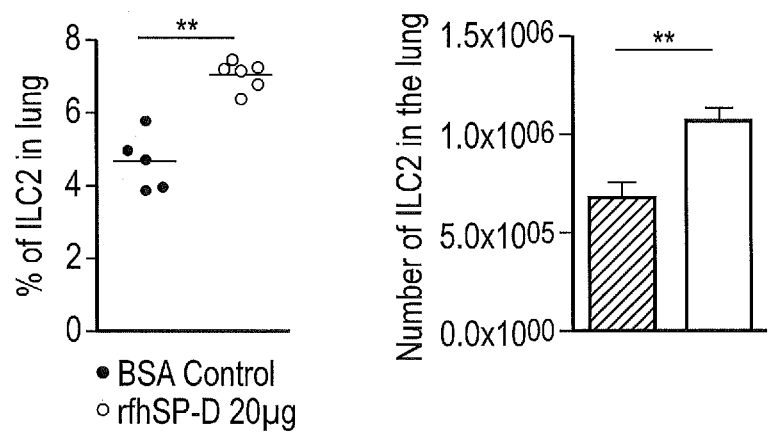

SF-D Treated Alveolar Macrophages Show Increased Alternative Activation and Confer Enhanced Protection to Nb Infection Alternatively activated macrophages (AAM) have been shown to be required for recall immunity against *Heligmosomoides polygyrus* and also for survival during Schistosomiasis. The inventors found this also was the case for recall immunity to Nb; mice deficient for IL-4Rα on macrophages (LysM$^{Cre}$IL-4R$^{-/lox}$) had an impaired ability to control secondary Nb infection (FIG. 3A). This suggested that enhanced SP-D mediated immunity to Nb may be a result of SP-D interaction with alveolar macrophages.

SP-D enhanced alternative activation of alveolar macrophages; intranasal SP-D treatment increased expression of the AAM markers YM1 and Relmα in CD11c$^+$SiglecF$^+$ AF$^{high}$ alveolar macrophages when compared to BSA treated control mice (FIG. 3B).

The inventors then directly tested whether SPD could enhance alternative activation of alveolar macrophages isolated from naïve mice. Naïve alveolar macrophages were artificially polarized to AAM by ex vivo culture with IL-4/IL-13 in the presence or absence of SP-D. Co-culture with SP-D resulted in increased YM1 and Relmα expression when compared to macrophages treated with only IL-4/IL-13 (FIG. 3C).

The inventors isolated alveolar macrophages from Nb infected SP-D treated or untreated mice and intra-nasally transferred to naïve mice. Recipients of SP-D treated macrophages had reduced intestinal worm burdens when compared to recipients of untreated macrophages (FIG. 3D). This suggests that SP-D-enhanced protection against Nb infection is partly at least mediated by an enhanced AAM protective response.

The inventors also investigated whether SP-D modulated the development of other immune cells responses. It was found that protection correlated with an increase in numbers of innate lymphoid type 2 cells (ILC2) in SP-D treated mice (FIG. 3E). ILC2s are newly identified innate cells that have been shown to play a crucial role in protection against helminth infections by inducing IL-13 cytokine responses.

Example 5

SP-D Binds to L4 Larval Stage of Nb

The inventors examined if SP-D could directly interact with Nb.

Figure 4:
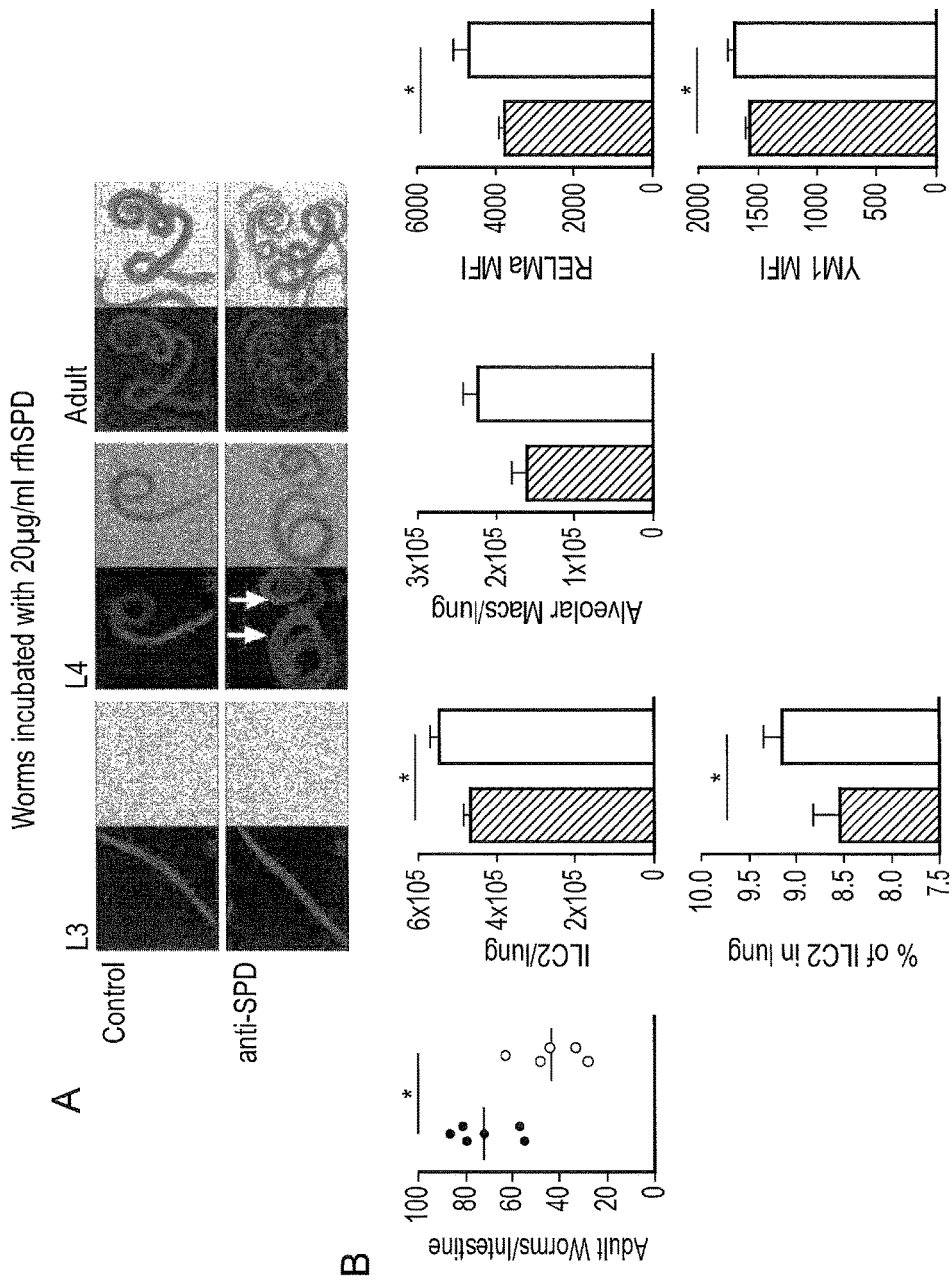
FIG. 4: SP-D binds to L4 stage of N. brasiliensis. (a) Confocal microscopic images of L3, L4 (lung) and L5 stage (intestine) of N. brasiliensis that were incubated with 20 µg/ml of rfhSP-D followed by staining with antibody to rfhSP-D. (b) 250 L4 stage larvae, coated or uncoated with rfhSP-D were intra-nasally administered into naïve mice. Intestinal worm burden were quantified at day 4 P.I. Numbers of ILC2 and alternatively activated macrophages were also assessed. Data are representative of one or two individual experiments. N=5 mice per group. *P<0.05.

Confocal microscopy was used to demonstrate SP-D's ability to directly bind Nb L3, L4 larvae and also to the adult worm. SP-D binding was restricted to the surface of Nb L4 larval stage (FIG. 4A). Nb L4 are the lung associated stage of the parasite life cycle. This data shows that, in addition to driving TH2 associated pulmonary immunity to Nb, SP-D also acts as an interface between Nb L4 and cells of the pulmonary immune system. To test this, the inventors intra-nasally infected naïve mice with either Nb L4 coated with recombinant SP-D or uncoated Nb L4. Analysis of host intestinal parasite burdens at day 5 P.I revealed significantly reduced parasite numbers in mice intra-nasally infected with SP-D coated L4 stage larvae when compared to mice infected with uncoated L4 larvae (FIG. 4B). Moreover, mice showing enhanced protection had increased numbers of ILC2 cells and alternatively activated macrophages. These results suggest that SP-D binding to Nb L4 enhances host ability to control infection.

Figure 6:
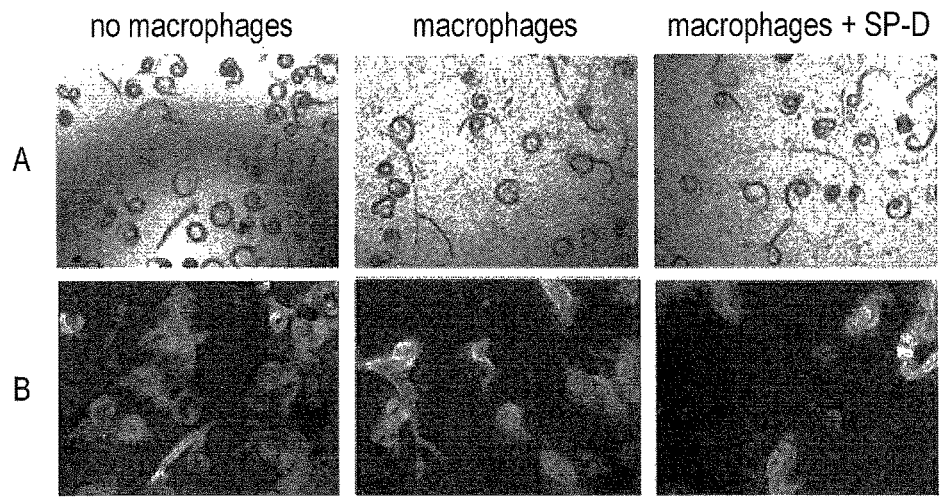
FIG. 6: SP-D has an opsonic effect on macrophage ability to kill L4 Nb. A) Light microscopy, 10× magnification of N.b L4 (no macrophages), L4+alveolar macrophages (macrophages) and SP-D coated (20 µg/ml) L4+alveolar macrophages (macrophages+SP-D); B) Overlay of 20 sequence pictures of each well shown above, calculated SD of movement (FIJI software): white indicates moving L4, resting/dead L4 appear black (fade to background); C) Live L4:dead L4 ratio.
Figure 6:
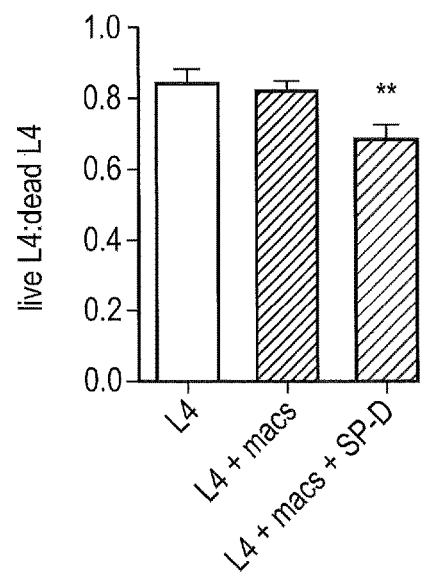

When SP-D and macrophages derived from Nb infected lungs were added to L4 Nb there was a significant decrease in the ratio of live:dead worms (FIG. 6). L4 Nb incubated with only macrophages derived from Nb infected lungs did not result in increased worm death. This is demonstrated by an equivalent ratio of live to dead L4 Nb found when comparing L4 Nb incubated with macrophages alone with L4 Nb only control.

This data indicates that SP-D has an opsonic effect on macrophage ability to kill L4 Nb (FIG. 6).

Example 6

SP-D Requires Carbohydrate Binding Head Region for its Optimal Function

Figure 5:
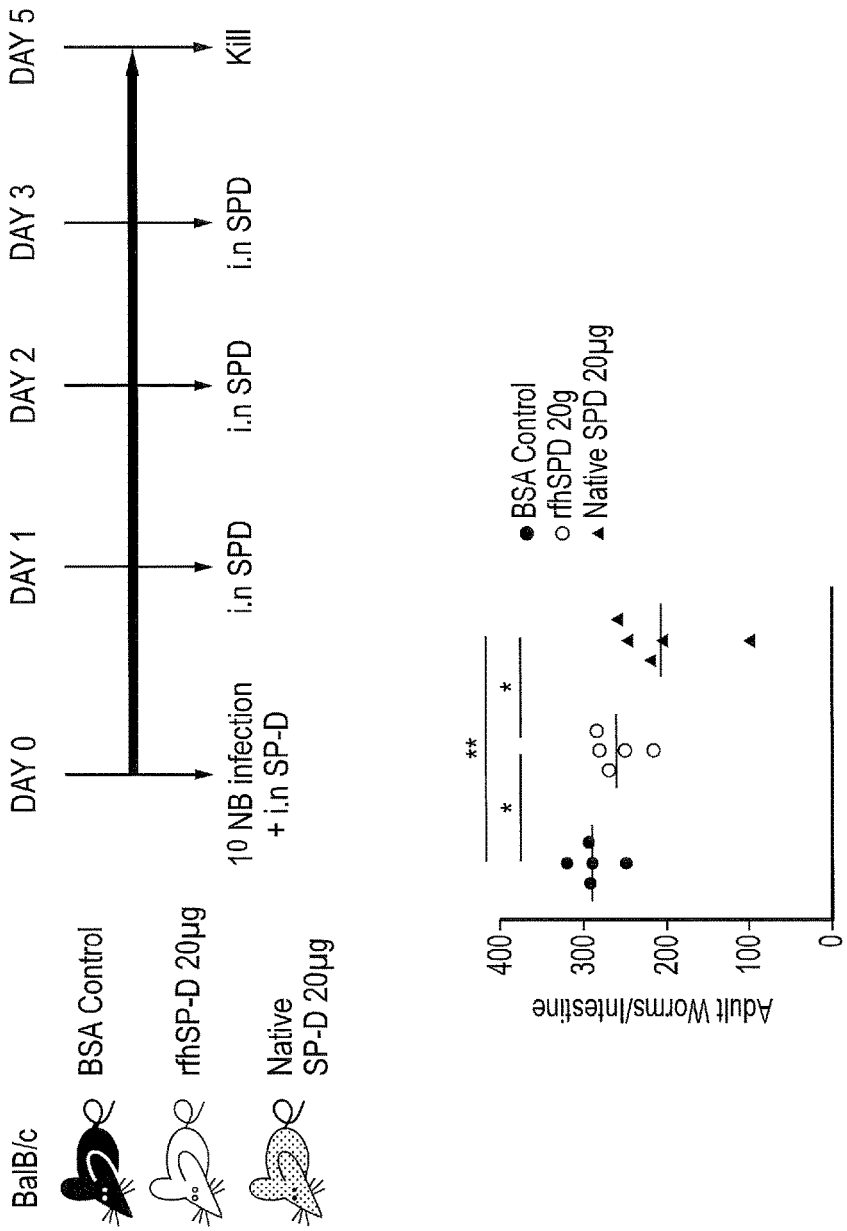
FIG. 5: Native SP-D can enhance SP-D mediated protection. Mice were intra-nasally treated with BSA, rfhSPD or native SPD and worms were quantified at 5 days P.I. Data are representative of two individual experiments. N=5-6 mice per group. *P<0.05, **P<0.01.

In this study, the inventors made use of the truncated recombinant fragment of human SPD, which lacks the N-terminal tail region and consists only of a short region of the collagen stalk, followed by the neck and the globular CRD region. In order to assess if differences in function existed between the rfhSPD and native SP-D, each was intra-nasally administered and worm burden was quantified at day 5 P.I (FIG. 5). The inventors found enhanced protection to Nb when treated with native SP-D than rfhSP-D.

Material & Methods

Animals Used 6-10-week-old mice were obtained from the University of Cape Town specific-pathogen-free animal facility. All experimental procedures were approved by the University of Cape Town Animal Ethics Committee. BALB/c background macrophage/neutrophil cell-specific IL-4Rα deficient mice (LysM$^{Cre}$IL-4Rα$^{-/lox}$) were generated as previously described and hemizygous IL-4Rα$^{-/lox}$ mice were used as controls.

N. brasiliensis Infection

Mice were inoculated subcutaneously with 500 N. brasiliensis L3 larvae suspended in 0.65%-0.9% NaCl using a 21G needle (Braun, Melsungen, Germany).

Adult worm burdens were determined by removing the small intestine and exposing the lumen by dissection. The intestines were incubated at 37° C. for 4 hours in 0.65% NaCl to allow the worms to migrate out after which the numbers of worms were counted under a dissecting microscope (Nikon Eclipse).

Viable motile L4 stage larvae of N. brasiliensis were isolated by finely cutting 2-day post-infected lung tissues, placing on sterile gauze and suspending them in a 50 ml centrifuge tube containing PBS at 37° C. for at least 3 hours. Viable worms migrated to the bottom of the tube and counted under a dissecting microscope (Nikon Eclipse).

Infection of mice with L4 worms was achieved by intranasal administration of 250 viable L4 worms in a 50 μl droplet to lightly anesthetized mice.

Administration of rfhSP-D or BSA

For administration of SP-D, mice were lightly anesthetized before 20 □g of SP-D or BSA was intra-nasally applied in 50 μl of PBS using sterile micropipette. Mice were held upright until all of the fluid was inhaled.

Preparation of Single Cell-suspension of Lung Tissue

Whole lung was removed from individual mice, finely cut and digested in Iscove's modified Eagle medium (IMDM) (Invitrogen) containing 50 U/ml collagenase type I (Invitrogen) and 13 μg/ml DNase (Roche) at 37° C. for 90 mins. Digested lung tissue were pushed through 70 or 100 μm nylon cell strainer (Becton Dickson, N.J.) and subjected to red cell lysis.

Flow Cytometry $1 \times 10^6$ single cell suspensions from individual lungs were stained in MACS buffer with lineage markers PE (CD3, CD19, CD11b, FceR1, Ter119, CD4, CD8, B220, Ly6G/6C), anti-CD127 PE-Cy7, anti-SCA-1 V450, anti-T1/ST2 FITC (DJ8) and anti-ICOS-biotin-Strep-Qdot antibodies to stain for Innate lymphoid Type 2 cells (ILC2). To stain for alveolar macrophages, cells were stained with anti-CD11c APC, anti-Siglec F PE. For intracellular staining of alternative activation markers, cells were fixed with 2% PFA, permeabilized with 0.1% saponin buffer and stained with anti-YM1 biotin and goat anti-Relmα followed by staining with Strep-Qdot and Rabbit anti-goat Alexa 488 respectively. Anti-FcR (2.4G2) was used to block non-specific binding of immunoglobulins to the FCγII/III receptors. Cells were acquired using FORTESSA Flow cytometer (BD Biosciences) and the data analyzed using Flowjo software (Tree star, inc., Ashland, Oreg., USA). Antibodies were purchased from BD Pharmingen, San Diego, Calif. or MD Bioproducts.

BAL Fluid and Serum

Mice were sacrificed at specific time points following infection. Approximately 500 μl of blood was collected by cardiac puncture and the serum isolated before being stored at −80° C. until further analysis.

Mice underwent BAL with sterile PBS containing 0.25 mM EDTA. The lungs were lavaged with 1 ml 3 times. BAL fluid was centrifuged at 1200 rpm for 5 mins and the supernatant was frozen at −80° C.

Enzyme-linked Immunosorbent Assay (ELISA) Analysis

BAL fluid and serum from N. brasiliensis infected mice were analyzed for SP-D content by ELISA. 96-well flat-bottom plates (Nunc Maxisorp; Thermo Fisher Scientifica, Roskilde, Denmark) were coated overnight at 4° C. with 50 μl of Rb-anti-mouse SPD antibody that was diluted in 1×PBS. The plates were then washed four times in wash buffer and subsequently blocked with 200 μl blocking buffer at 37° C. for 3 hours. Following this, three-fold dilutions (1/160, 1/480 and 1/1440) of the samples and standards were prepared in dilution buffer and the diluted samples and standards were loaded into wells and incubated overnight at 4° C. The plates were further washed and 50 μl of biotinylated Rb-anti-mouse SPD antibody was diluted in dilution buffer and added and incubated at 37° C. for 3 hrs. 50 μl of Streptavidin-coupled horseradish peroxidase (HRP) (1/10000 dilution) was added after washing the plates and left in the incubator for 1 hour at 37° C. The plates were developed with TMB microwell peroxidase substrate system, and the reaction was stopped with 1M $H_3PO_4$. The plates were read at an absorbance of 450 nm using a VersaMax microplate reader (Molecular Devices Corporation, Sunnyvale, Calif., U.S.A). All antibodies were from BD Pharmingen, San Diego, Calif.

Adoptive Transfer Experiments

Mice were treated with 20 μg of SP-D or BSA at D0, 1, 2, 3, 6 and 7 post-infection. Single-cell suspensions of pooled lungs were prepared at day 8 post-infection and alveolar macrophages were stained with anti-CD11c APC-conjugated and anti-Siglec F PE conjugated monoclonal antibody (MAb) (BD Pharmingen) before they were isolated (>95% purity) as CD11c$^+$Siglec F$^+$ Autoflourscent$^{high}$ using a FACSVantage cell sorter (Becton Dickinson). 1×10$^5$ macrophages were then transferred intra-nasally in to naïve BALB/c mice 24 hours prior to N. brasiliensis infection.

Cytospin Preparations of Alveolar Macrophages

To confirm the morphology of the isolated macrophages, cytospin slides were prepared and stained using the Rapid-diff staining kit.

In Vitro Culture of Macrophages with SP-D

Naïve alveolar macrophages (CD11C$^+$SiglecF$^+$AF$^{high}$) were isolated from single cell suspensions of lung tissue by FACSARIA and plated in duplicates at 4×10$^5$ cells per well. Cells were stimulated with either recombinant mouse IL-4/IL-13, IL-4/IL-13+20 μg/ml of rfhSPD or left untreated. The cultures were incubated for 60 hrs at 37° C. Thereafter, cells were washed and stained for alternative activation markers, YM1 and Relmα as described above, before acquisition with FORTESSA flow cytometer.

Confocal Microscopy

L3, L4 and adult stage larvae of N. brasiliensis were fixed overnight in 2% paraformaldehyde at 4° C. The larvae were extensively washed using PBS containing 0.2% BSA and 1 mM CaCl$_2$. Non-specific binding was blocked by incubation of the larvae in 0.2% BSA in PBS for 1 hr at room temperature. Thereafter, the larvae were incubated with 20 μg/ml SPD in PBS containing 0.2% BSA and 1 mM CaCl$_2$ for 1 hr at 32° C. After extensive washing, the larvae were incubated with biotinylated rabbit anti-rfhSPD (1/200) antibody overnight at 4° C. To detect the SP-D binding, the organisms were subsequently incubated with streptavidin cy3 (1/500). Organisms were mounted on to slides using mowiol containing anti-fading reagent. All sections were viewed with a Zeiss Axiovert LSM 510 Meta NLO microscope.

Statistics

Data were expressed as mean±standard deviation and analyzed using one-tailed Mann-Whitney nonparametric T test with a 95% confidence interval. P-Value<0.05 were considered significant and are indicated by an asterisk.

The invention claimed is:

1. A method for treatment and/or prevention of a parasitic infection in a subject, comprising a step of administering Surfactant Protein D (SP-D), or a fragment, homologue, variant or derivative thereof, to the subject, wherein the SP-D, or the fragment, homologue, variant or derivative thereof, is administered to the lungs of the subject, and wherein the parasite is a parasitic helminth.

2. The method according to claim 1, wherein SP-D comprises the sequence shown in SEQ ID NO: 1, or the SP-D fragment, homologue, variant or derivative comprises an amino acid sequence having at least 70% sequence identity over at least 50 amino acid residues of SEQ ID NO: 1.

3. The method according to claim 1, wherein the SP-D fragment comprises the sequence shown in SEQ ID NO: 3, or the SP-D fragment, homologue, variant or derivative comprises an amino acid sequence having at least 70% sequence identity over at least 50 amino acid residues of SEQ ID NO: 3.

4. The method according to claim 1, wherein SP-D, or the fragment, homologue, variant or derivative thereof, has carbohydrate binding activity.

5. The method according to claim 1, wherein SP-D, or the fragment, homologue, variant or derivative thereof, reduces the parasite burden.

6. The method according to claim 1, wherein SP-D, or the fragment, homologue, variant or derivative thereof, enhances alternative activation of alveolar macrophages.

7. The method according to claim 1, wherein SP-D, or the fragment, homologue, variant or derivative thereof, induces innate lymphoid type 2 cells.

8. The method according to claim 1, wherein SP-D, or the fragment, homologue, variant or derivative thereof, acts as an opsonin of the parasite.

9. The method according to claim 1, wherein a lifecycle of the parasite involves infestation of the lungs of the subject.

10. The method according to claim 1, wherein the parasite is a parasitic nematode.

11. The method according to claim 1, wherein the subject is a mammal.

12. The method according to claim 1, wherein the SP-D, or the fragment, homologue, variant or derivative thereof, is administered intranasally.

13. The method according to claim 1, wherein the SP-D, or the fragment, homologue, variant or derivative thereof, is administered in combination with an anti-parasite therapy.

14. The method according to claim 13 wherein the anti-parasite therapy is an anti-nematode therapy selected from the group consisting of albendazole, mebendazole, thiabendazole, ivermectin, piperazine, pyrantel pamoate, and levamisole.

* * * * *